United States Patent
Hsieh et al.

(10) Patent No.: US 9,521,982 B2
(45) Date of Patent: *Dec. 20, 2016

(54) COMPUTED TOMOGRAPHY SYSTEM WITH DYNAMIC BOWTIE FILTER

(71) Applicant: The Board of Trustees of the Leland Stanford Junior University, Palo Alto, CA (US)

(72) Inventors: Scott Hsieh, Anaheim, CA (US); Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/333,459

(22) Filed: Jul. 16, 2014

(65) Prior Publication Data

US 2014/0328453 A1   Nov. 6, 2014

Related U.S. Application Data

(63) Continuation-in-part of application No. 14/301,195, filed on Jun. 10, 2014, and a continuation-in-part of
(Continued)

(51) Int. Cl.
*G21K 1/10* (2006.01)
*A61B 6/06* (2006.01)
(Continued)

(52) U.S. Cl.
CPC ............ *A61B 6/405* (2013.01); *A61B 6/035* (2013.01); *A61B 6/06* (2013.01); *A61B 6/4035* (2013.01);
(Continued)

(58) Field of Classification Search
CPC ........... A61B 6/00; A61B 6/06; A61B 6/4035; A61B 6/4042; A61B 6/405; A61B 6/44; G21K 1/00; G21K 1/02; G21K 1/10; G21K 2210/00; G21K 2201/00; G02B 5/20; G02B 5/201; G02B 5/22; G02B 5/2223; G02B 26/00; G02B 26/02; G02B 26/023
(Continued)

(56) References Cited

U.S. PATENT DOCUMENTS 3,660,664 A * 5/1972 Pasmeg .................... 378/159
4,445,226 A * 4/1984 Brody .................... 378/98.9
(Continued)

FOREIGN PATENT DOCUMENTS

JP  07008483    1/1995
JP  2010-511857  4/2010
(Continued)

OTHER PUBLICATIONS

Graham, S.A., et al. "Compensators for Dose and Scatter Management in Cone-beam Computed Tomography", Jul. 2007, American Association of Physicists in Medicine, Medical Physics: vol. 34 (7), pp. 2691-2703.*

(Continued)

*Primary Examiner* — Anastasia Midkiff
(74) *Attorney, Agent, or Firm* — Beyer Law Group LLP

(57) ABSTRACT

A CT apparatus for scanning an object is provided. An x-ray source is provided, wherein the x-ray source provides a collimated x-ray beam with a cross-section. A plurality of attenuation elements is provided between the source and object. An actuator is connected to the attenuation elements for moving the attenuation elements. An x-ray detector is located on an opposite side of the object from the x-ray source and is for detecting x-rays that pass through the object and the plurality of attenuation elements. A gantry (Continued)

rotates the x-ray source, the plurality of attenuation elements, and the x-ray detector around an axis of rotation.

24 Claims, 15 Drawing Sheets

Related U.S. Application Data application No. 14/125,926, filed as application No. PCT/US2012/042469 on Jun. 14, 2012.

(60) Provisional application No. 61/833,719, filed on Jun. 11, 2013, provisional application No. 61/498,175, filed on Jun. 17, 2011, provisional application No. 61/589,245, filed on Jan. 20, 2012, provisional application No. 61/847,490, filed on Jul. 17, 2013, provisional application No. 61/847,487, filed on Jul. 17, 2013, provisional application No. 61/871,248, filed on Aug. 28, 2013, provisional application No. 61/905,761, filed on Nov. 18, 2013, provisional application No. 61/871,627, filed on Aug. 29, 2013.

(51) Int. Cl.
| | |
|---|---|
| *G02B 5/20* | (2006.01) |
| *G02B 5/22* | (2006.01) |
| *G02B 26/02* | (2006.01) |
| *A61B 6/00* | (2006.01) |
| *A61B 6/03* | (2006.01) |

(52) U.S. Cl.
CPC ............ *G02B 5/201* (2013.01); *G02B 26/023* (2013.01); *G21K 1/10* (2013.01); *A61B 6/4042* (2013.01); *A61B 6/44* (2013.01); *G02B 5/20* (2013.01); *G02B 5/22* (2013.01); *G02B 26/02* (2013.01)

(58) Field of Classification Search
USPC ... 378/4, 16, 20, 62, 91, 145, 156–159, 204, 378/210; 359/885, 889–892
See application file for complete search history.

(56) References Cited

U.S. PATENT DOCUMENTS

| | | | | |
|---|---|---|---|---|
| 4,916,727 A | * | 4/1990 | Sheridan | 378/207 |
| 4,980,904 A | * | 12/1990 | Sones et al. | 378/207 |
| 5,247,559 A | * | 9/1993 | Ohtsuchi et al. | 378/53 |
| 5,335,260 A | * | 8/1994 | Arnold | 378/207 |
| 5,625,665 A | * | 4/1997 | Fokkink et al. | 378/156 |
| 6,359,969 B1 | * | 3/2002 | Shmaenok | 378/156 |
| 6,501,828 B1 | * | 12/2002 | Popescu | 378/150 |
| 6,920,203 B2 | * | 7/2005 | Short et al. | 378/147 |
| 7,076,029 B2 | | 7/2006 | Toth et al. | |
| 7,260,182 B2 | | 8/2007 | Toth et al. | |
| 7,330,535 B2 | * | 2/2008 | Arenson et al. | 378/158 |
| 7,333,587 B2 | * | 2/2008 | De Man | A61B 6/032 378/16 |
| 7,433,443 B1 | | 10/2008 | Tkaczyk et al. | |
| 7,630,477 B2 | | 12/2009 | Toth et al. | |
| 7,634,045 B2 | | 12/2009 | Popescu | |
| 7,706,508 B2 | | 4/2010 | Arenson et al. | |
| 7,796,725 B1 | | 9/2010 | Wu et al. | |
| 8,412,308 B2 | | 4/2013 | Goldbach | |
| 9,006,677 B2 | | 4/2015 | Al-Sadah et al. | |
| 2003/0198319 A1 | | 10/2003 | Toth et al. | |
| 2003/0199757 A1 | | 10/2003 | Toth et al. | |
| 2004/0105526 A1 | | 6/2004 | Zhang et al. | |
| 2004/0179646 A1 | | 9/2004 | Li et al. | |
| 2004/0225222 A1 | | 11/2004 | Zeng et al. | |
| 2005/0013411 A1 | | 1/2005 | Yahata et al. | |
| 2005/0031084 A1 | | 2/2005 | Toth et al. | |
| 2005/0089137 A1 | | 4/2005 | Toth et al. | |
| 2005/0089146 A1 | | 4/2005 | Toth et al. | |
| 2006/0198496 A1 | | 9/2006 | Toth et al. | |
| 2007/0092066 A1 | * | 4/2007 | Tkaczyk | G21K 1/10 378/156 |
| 2009/0218521 A1 | * | 9/2009 | Sogard et al. | 250/504 R |
| 2010/0061513 A1 | * | 3/2010 | Muto | 378/82 |
| 2010/0308229 A1 | | 12/2010 | Bertram et al. | |
| 2011/0206259 A1 | * | 8/2011 | Mistretta et al. | 382/131 |
| 2014/0192950 A1 | | 7/2014 | Pelc et al. | |
| 2014/0294141 A1 | | 10/2014 | Hsieh et al. | |

FOREIGN PATENT DOCUMENTS

| | | |
|---|---|---|
| JP | 4550179 | 7/2010 |
| WO | WO 2012/174246 A2 | 12/2012 |

OTHER PUBLICATIONS

Mail, N., et al. "The Influence of Bowtie Filtration on Cone-beam CT Image Quality", Jan. 2009, American Association of Physicists in Medicine, Medical Physics: vol. 36 (1), pp. 22-32.*
Wunderlich, Adam, et al., "Achieving Uniform Noise in Direct Fan-beam CT Reconstruction Through Bowtie Filter Design", 2007, IEEE, 2007 IEEE Nuclear Science Symposium Conference Record, M26-180, pp. 4379-4382.*
Office Action dated Jul. 31, 2015 from U.S. Appl. No. 14/125,926.
Office Action dated Aug. 19, 2015 from U.S. Appl. No. 14/301,195.
Hsieh et al., "Control algorithms for dynamic attenuators," Med Phys. 41(6): 061907; 2014; 17 pages.
Hsieh et al., "The feasibility of a piecewise-linear dynamic bowtie filter," Med Phys. 40(3):031910; 2013; 12 pages.
International Search Report dated Feb. 1, 2013 from International Application No. PCT/US2012/042469.
Final Office Action dated Jan. 11, 2016 from U.S. Appl. No. 14/125,926.
Final Office Action dated Jan. 29, 2016 from U.S. Appl. No. 14/301,195.
Notice of Allowance dated Mar. 28, 2016 from U.S. Appl. No. 14/125,926.

* cited by examiner

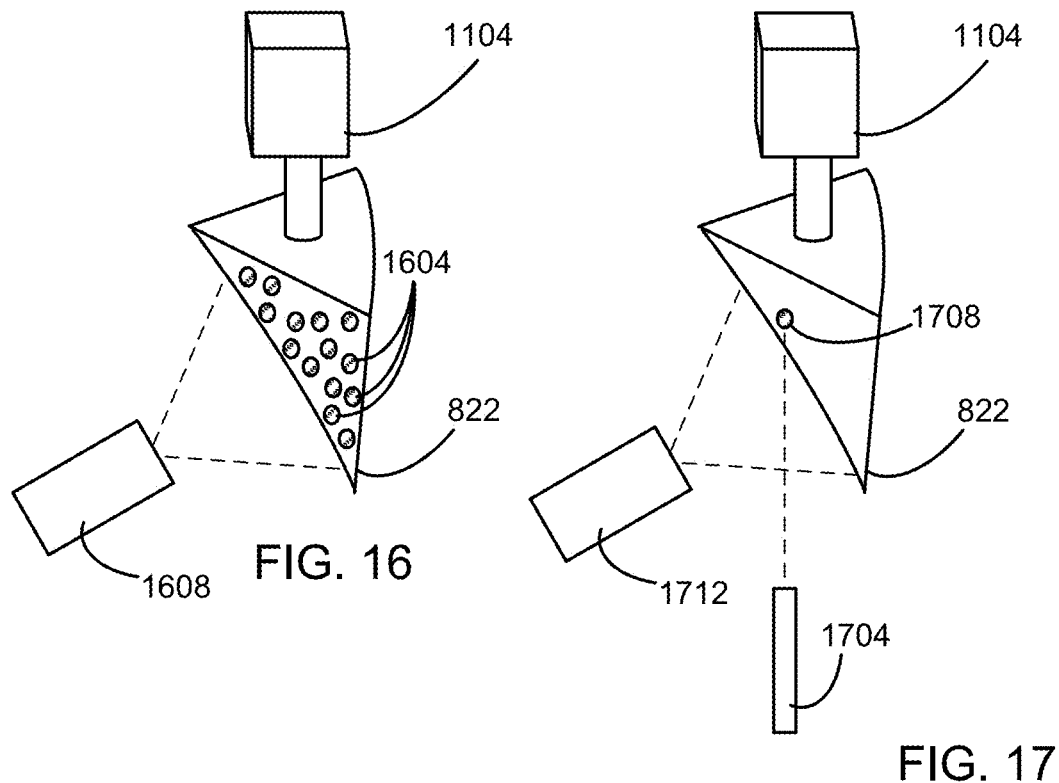
FIG. 16
FIG. 17
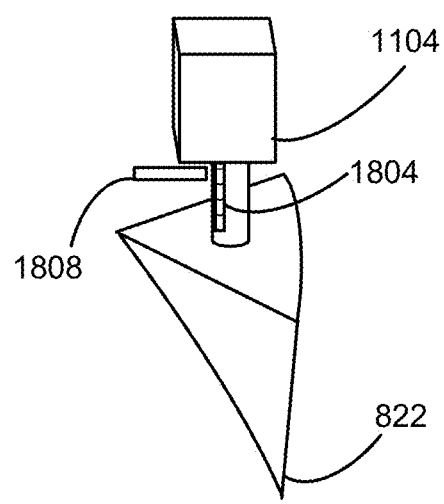
FIG. 18

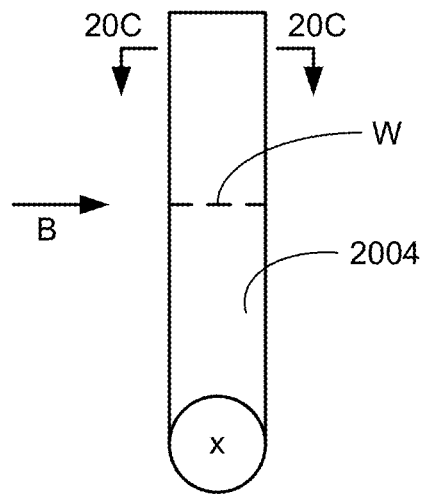
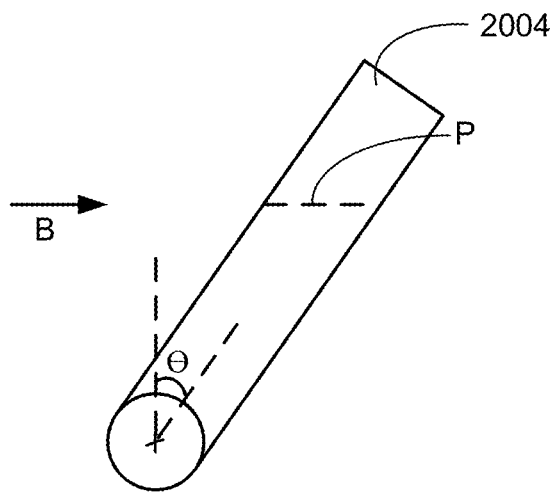
FIG. 20A  FIG. 20B
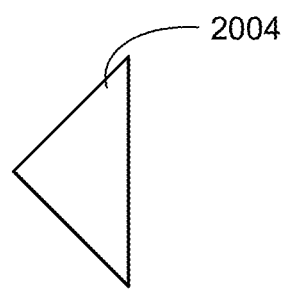
FIG. 20C
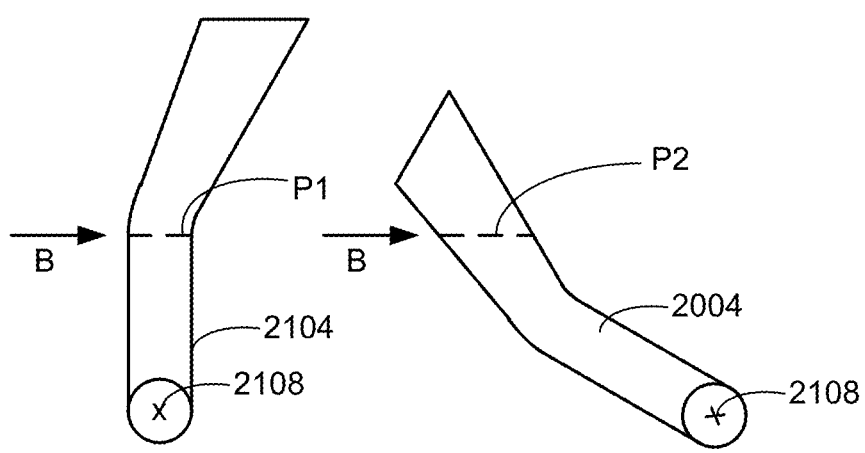
FIG. 21A  FIG. 21B

COMPUTED TOMOGRAPHY SYSTEM WITH DYNAMIC BOWTIE FILTER

CROSS REFERENCE TO RELATED APPLICATIONS

This application is a continuation-in-part under 35 U.S.C. §120 of U.S. patent application Ser. No. 14/301,195, filed on Jun. 10, 2014, entitled COMPUTED TOMOGRAPHY SYSTEM WITH DYNAMIC BOWTIE FILTER, by Pelc et al., which claims priority to U.S. Provisional Patent Application No. 61/833,719, filed Jun. 11, 2013, entitled COMPUTED TOMOGRAPHY SYSTEM WITH DYNAMIC BOWTIE FILTER. U.S. patent application Ser. No. 14/301,195 is also a continuation-in-part under 35 U.S.C. §120 of U.S. patent application Ser. No. 14/125,926, filed on Mar. 11, 2014, entitled COMPUTED TOMOGRAPHY SYSTEM WITH DYNAMIC BOWTIE FILTER, by Pelc et al., which is a National Stage Entry of PCT/US2012/042469 filed on Jun. 14, 2012, entitled COMPUTED TOMOGRAPHY SYSTEM WITH DYNAMIC BOWTIE FILTER, which claims priority to U.S. Provisional Patent Application No. 61/498,175, filed Jun. 17, 2011, entitled SIMULATION OF A DYNAMIC BOWTIE and U.S. Provisional Patent Application No. 61/589,245, filed Jan. 20, 2012, entitled SUPPORTING MATERIAL FOR THE CALIBRATION AND WEDGE DESIGN FOR DYNAMIC BOWTIE. This application further claims priority under 35 U.S.C. §119 from U.S. Provisional Patent Application No. 61/847,490, filed Jul. 17, 2013, entitled WEDGE GEOMETRY FOR A DYNAMIC ATTENUATOR IN CT; U.S. Provisional Patent Application No. 61/847,487, filed Jul. 17, 2013, entitled CONTROL METHODS FOR DYNAMIC ATTENUATORS IN CT; U.S. Provisional Patent Application No. 61/871,248, Aug. 28, 2013, entitled K-EDGE MATERIAL SELECTION FOR DYNAMIC ATTENUATORS IN CT; U.S. Provisional Patent Application No. 61/871,627, filed Aug. 29, 2013, entitled ROTATING DESIGN FOR A PIECEWISE-LINEAR DYNAMIC ATTENUATOR IN CT; and U.S. Provisional Patent Application No. 61/905,761, filed Nov. 18, 2013, entitled FLUID-FILLED DESIGNS OF DYNAMIC ATTENUATORS FOR CT IMAGING. All of the foregoing applications are incorporated herein by reference for all purposes.

GOVERNMENT RIGHTS

This invention was made with Government support under contracts EB006837, EB015574 and 1R21EB01557401A1 awarded by the National Institutes of Health. The Government has certain rights in this invention.

STATEMENT OF GOVERNMENT FUNDED RESEARCH

This invention was made with Government support under FA9550-05-C-0059 awarded by DoD, Air Force Office of Scientific Research, National Defense Science and Engineering Graduate (NDSEG) Fellowship, 32 CFR 168a.

BACKGROUND OF THE INVENTION

This invention relates generally to computed tomography (CT).

SUMMARY OF THE INVENTION

In accordance with the invention, a CT apparatus for scanning an object is provided. An x-ray source is provided, wherein the x-ray source provides a collimated x-ray beam with a cross-section with a length and thickness. A plurality of wedges is provided between the source and object, where the plurality of wedges comprises a first plurality of wedges and a second plurality of wedges, wherein each wedge of the first plurality of wedges has a thickness that increases in a first direction of movement by the actuators and each wedge of the second plurality of wedges has a thickness that decreases in the first direction. An actuator is connected to the wedges for moving the wedges substantially perpendicular to the length of the cross-section of the collimated x-ray beam. An x-ray detector is located on an opposite side of the object from the x-ray source and is for detecting x-rays that pass through the object and the plurality of wedges. A gantry rotates the x-ray source, the plurality of wedges, and the x-ray detector around an axis of rotation.

In another manifestation of the invention, a CT apparatus for scanning an object is provided. An x-ray source is provided, wherein the x-ray source provides a collimated x-ray beam with a cross-section with a length and thickness. A plurality of filter elements is provided comprising a K-edge filter material between the source and object, wherein the K-edge filter material provides a K-edge above 20 KeV. An actuator is connected to the filter elements for moving the filter element to change a cross-sectional path length of the collimated x-ray beam through the filter element. An x-ray detector is located on an opposite side of the object from the x-ray source and is for detecting x-rays that pass through the object and the plurality of filter elements. A gantry rotates the x-ray source, the plurality of filter elements, and the x-ray detector around an axis of rotation.

In another manifestation of the invention, a CT apparatus for scanning an object is provided. An x-ray source is provided, wherein the x-ray source provides a collimated x-ray beam with a cross-section with a length and thickness. A plurality of attenuating elements is provided between the source and object. An actuator is connected to each attenuating element of the plurality of attenuating elements for individually rotating a plurality of attenuating elements, wherein the rotation changes path lengths of the x-ray beam through each attenuating element of the plurality of attenuating elements. An x-ray detector is located on an opposite side of the object from the x-ray source and is for detecting x-rays that pass through the object and the plurality of attenuating elements. A gantry rotates the x-ray source, the plurality of attenuating elements, and the x-ray detector around an axis of rotation.

In another manifestation of the invention, a method of creating a CT image is provided. X-rays are provided from an x-ray source with a Hsieh-Pelc distribution. The x-rays are passed through an object. The x-rays that pass through the object are detected. The shape of the object and the distribution of the x-rays are used to create a CT image.

In another manifestation of the invention, a CT apparatus for scanning an object is provided. An x-ray source is provided, wherein the x-ray source provides a collimated x-ray beam with a cross-section with a length and thickness. A plurality of filter elements is provided comprising gas filled chambers. A pressure controller is provided for controlling gas pressures in the plurality of filter elements, wherein the pressure controller is able to provide different pressures in different filter elements of the plurality of filter elements, wherein the gas pressures are used to control attenuation. An x-ray detector is located on an opposite side of the object from the x-ray source and is for detecting x-rays that pass through the object and the plurality of filter elements. A gantry rotates the x-ray source, the plurality of filter elements, and the x-ray detector around an axis of rotation.

In another manifestation of the invention, a CT apparatus for scanning an object is provided. An x-ray source is provided, wherein the x-ray source provides a collimated x-ray beam with a cross-section with a length and thickness. A plurality of filter elements is provided wherein each filter element comprises at least one hollow chamber. A liquid controller is provided, which is able to fill and empty different filter elements with a liquid. An x-ray detector is located on an opposite side of the object from the x-ray source and is for detecting x-rays that pass through the object and the plurality of filter elements. A gantry rotates the x-ray source, the plurality of filter elements, and the x-ray detector around an axis of rotation.

The invention and objects and features thereof will be more readily apparent from the following detailed description and appended claims when taken with the drawings.

BRIEF DESCRIPTION OF THE DRAWINGS

FIG. 16 is a schematic view of a wedge with an actuator used in another embodiment.

FIG. 17 is a schematic view of a wedge with an actuator used in another embodiment.

FIG. 18 is a schematic view of a wedge with an actuator used in another embodiment.

FIGS. 20A-C are schematic illustrations of an embodiment with a rotating attenuation element.

FIGS. 21A-B show embodiments of the invention.

DETAILED DESCRIPTION OF ILLUSTRATED EMBODIMENTS

Figure 1:
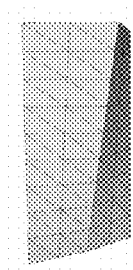
FIG. 1 shows three-dimensional renderings for a single wedge.

The bowtie filter in CT customizes the flux profile of the incident x-ray beam based on its fan angle. Traditionally, static bowtie filters are tailored only for very generic scans (e.g., head or body) and for the average patient. An embodiment of the invention provides a dynamic bowtie, which can present a time-dependent piecewise-linear attenuation profile in fan angle. This dynamic bowtie presents several advantages over traditional bowtie. An embodiment of the invention reduces the dynamic range on the detector. Using clinical datasets, we found that the dynamic range may be reduced by a factor of fifty in most parts of the body and by a factor of four in the most challenging regions. Such a reduction in dynamic range may be particularly welcome in applications involving photon-counting detectors. The radiation dose delivered remains comparable to the traditional bowtie, and the noise distribution of the image is made more uniform. Beam hardening artifacts resulting from the dynamic bowtie were analyzed and suppressed with a two-pass algorithm. Other potential advantages of the dynamic bowtie are provided, and include lower radiation dose to the patient and/or improved image quality.

It is often desirable to measure the different line integrals that CT measures with differing number of photons. Those line integrals that pass through clinically relevant regions or through highly attenuating tissue should be measured with more photons; conversely, rays that have little attenuation or which go through irrelevant or radiation sensitive tissue should be measured with fewer photons. Dose concerns aside, extra photons delivered to the wrong location may even degrade image quality if they contribute to excess scatter, or if a photon-counting detector (PCXD) is employed and count rate loss ensues. Ideally, it would be possible to take each ray in a sinogram and choose, on a ray-by-ray basis, how many photons are used to measure that line integral. Currently employed technologies provide us with comparatively limited ability to control flux.

The traditional bowtie filter is a pre-patient attenuator which attenuates photons as they leave the x-ray source and before they reach the patient, but with a static attenuation profile that does not vary in time. In other words, the bowtie filter provides a constant attenuation profile that is a function of fan angle but is constant for an entire volumetric scan. The bowtie filter is usually designed to compensate for the varying path length through the patient and helps to equalize the radiation incident on the detector, reducing the dynamic range on the detector. In reducing the dynamic range, the bowtie also reduces the scatter, which can be dominated by lightly attenuating regions. The radiation dose is also alleviated because the bowtie filter tends to selectively remove photons in regions where the noise statistics are already very good and for which additional photons would produce very little incremental benefit. One limitation of the bowtie filter is that the attenuation profile it produces is fixed and cannot change with time.

Tube current modulation is another technology which can control flux and is complementary to the bowtie filter in that it can modulate the photon flux as a function of time, but not of fan angle. Tube current modulation has the additional advantage of being quite flexible, and can be customized on a per-patient basis; the bowtie filter, in contrast, must be designed for a generic scan on a generic patient. Tube current modulation does not change the scatter to primary ratio, but can reduce the dynamic range and significantly improve dose efficiency. Together, the bowtie filter and tube current modulation give some control over the flux in both time and fan angle, but still leave room for improvement.

An embodiment of the invention provides a dynamic bowtie filter that is directed towards the goal of improved control of the x-ray flux. The embodiment is able to provide an attenuation profile that is piecewise linear in fan angle, and is able to dynamically morph as the gantry rotates. Previous dynamic bowtie designs have been reported in the patent literature, but they typically consist of only two or three moving parts and are often optimized for elliptical water cylinders. Such designs do not afford the level of flexibility of a piecewise-linear attenuation profile.

This extra flexibility would be especially beneficial for enabling photon-counting detectors, which currently suffer from inability to handle high count rates. When the incident flux is low compared to the count rate limitation, these detectors provide superior detective quantum efficiency (DQE) and intrinsic energy discriminating capabilities. As the incident flux increases, however, count rate loss and pulse pile-up occur, which damages the DQE and the energy information. The reduction in the dynamic range provided by a dynamic bowtie could be used to attenuate the rays where count rate loss and pulse pile-up are most significant, making photon-counting CT with detectors with relatively modest count rate limitation feasible. Besides its application to photon-counting detectors, a dynamic bowtie filter may provide superior scatter reduction, may be useful for reducing the dose of a scan without sacrificing diagnostic quality, and could additionally enable region-of-interest scans.

Design

An embodiment of the invention provides an attenuation profile that is piecewise linear in fan angle. Mathematically, a piecewise linear function can be achieved by using a basis set of triangle functions, regularly spaced in fan angle and with variable height. To be concrete, let us define $\Lambda(x)$ to be a triangle function, so that $\Lambda(x)=\max(0, 1-|x|)$. Now we introduce $f(x)$, defined as $$f(x) = \sum_{k=-\infty}^{\infty} c_k \Lambda\left(x - \frac{k}{z}\right)$$

This function can be set to become any piecewise linear function we desire (with piece length unity) by changing $c_k$.

In two dimensions, this mathematical notion can be translated into practice by taking advantage of the flexibility afforded via the third dimension. We use the fact that most multi-slice scanners have small beam thickness in the z-direction, and for now make the approximation that we are only looking at a single slice. Each triangle function $c_k\Lambda(k)$ can then be implemented using wedges of attenuating material whose cross-section is a triangle of a given size base but where the height of the triangle depends on position along the length of the wedge. The height of the wedge determines the width or thickness of material traversed by the x-ray beam. Any axial slice through the wedge would present a triangle function attenuation profile. By moving or scrolling the wedges up and down in the third dimension, we would scale the height of the triangle function presented. FIG. 1 shows three-dimensional renderings for a single wedge. Different axial slices present triangular-shaped attenuation profiles of different height. Moving the wedge up and down scales the height.

Figure 2A:
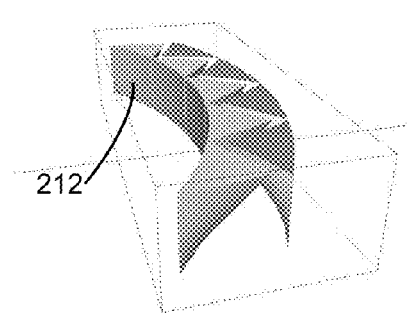
FIG. 2A shows a perspective view of an embodiment of the invention that uses two rows of wedges to form a dynamic bow tie.
Figure 2B:
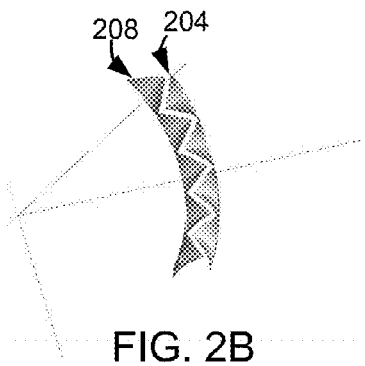
FIG. 2B shows a top view of the two rows forming the dynamic bow tie.

Building up the entire piecewise linear function $f(x)$ requires multiple overlapping triangular elements. The wedges cannot physically overlap, but the multiple triangular wedges can be grouped into two separate layers, one offset from the other by half of the triangle base. An x-ray beam would pass through both layers, and together would be attenuated by the piecewise linear function of the embodiment. FIG. 2A shows a perspective view of an embodiment of the invention that uses two rows of wedges to form a dynamic bowtie. FIG. 2B shows a top view of the two rows forming the dynamic bowtie. By moving each wedge separately we are able to build up the piecewise linear attenuation profile that we desire. In a fan beam CT scanner this assembly would be curved as part of a circle, and the x-ray source would be placed at the center of that circle. Other embodiments may have more than two rows of wedges.

In an embodiment of the invention, a dynamic bowtie would be placed a short distance away from the x-ray tube. This embodiment has the bowtie parameters found in the table below.

| Source-isocenter distance | 50 cm |
|---|---|
| Detector-isocenter distance | 50 cm |
| Source-bowtie distance | 8 cm |
| Number of triangular wedges | 15 |
| Width of each triangle | 11.4 mm |
| Material | Iron |
| Maximum depth of wedge | 6.1 mm |
| Axial height extent of wedge | 40 mm |
| Axial FOV of scan | 4 cm |
| Actuator speed | 25 cm/sec |

The choice of material is dependent on beam-hardening characteristics. The choice of material also changes the maximum height of the wedges which may be important from a manufacturing and space perspective.

Most multi-slice scanners capture several centimeters of data in z in a single scan. The bowtie, as presented, will produce an attenuation profile that is linear in z. This can be corrected for with the use of a slanted compensator, which has a constant thickness in fan angle but is slanted in z to counteract the effect of the existing slant. Together, the bowtie filter plus the compensator will produce an overall attenuation that is constant in z. This is acceptable for most current CT systems because a typical CT system today has an in-plane field of view that is much longer than its axial field of view. Other variations on this design may allow variation of attenuation in the z direction. Depending on the goals of the scan, the compensator may not be necessary; or, portions of the compensator may be withdrawn in order to increase the flux in some parts of the x-ray fan beam. Likewise, some of the wedges may be withdrawn from the beam so as to allow maximum flux to penetrate the object.

It would is simple to extend the concept of the present invention to other basis functions besides triangles and thereby build up more general splines in other embodiments of the invention. The extension to other basis functions could include, as one example, smoothed triangle functions, which would create an attenuation function that is even smoother than piecewise linear and may produce fewer artifacts.

From a physical standpoint, the parameters in Table 1 were chosen so the dynamic bowtie filter in the embodiment of the invention can be immediately actionable. The wedges in this embodiment are relatively easy to manufacture and work with, and would provide the ability to attenuate a typical CT x-ray beam by up to three orders of magnitude. If it were more convenient to make the bowtie smaller or larger, the choice of wedge material would simply change. The speed of the motors which are used to scroll the wedges are another design consideration, and they should be chosen in conjunction with the angle of the wedge; together, these parameters determine the speed at which the dynamic bowtie is able to morph with time. Larger angles permit a more agile piecewise linear attenuation profile, but they introduce more variation in the z-direction. A dynamic bowtie employing more actuators and faster motors would obviously provide superior dynamic ability, but other embodiments are simpler to build.

Calibration of the dynamic bowtie is challenging but desirable and possible. It is not important to have extremely precise control over the position of each wedge in the bowtie, but it is imperative that the position of the wedges be known. The conversion of the measured intensity to a line integral of attenuation needs knowledge of the incident intensity, and this is affected by the wedge positions. The beam hardening correction also needs to be adjusted on a per-ray basis using the known wedge profiles in a manner than is known in the art, for example as described below. Based on these facts and the parameters listed in the table, the dynamic bowtie is quite actionable and practical with today's technology.

Methods

In a simulation of an embodiment of the invention, we sought to quantify the ability of the embodiment of the invention, especially with interest in the performance of the bowtie in more difficult settings, such as a thorax cross-section with sharp transitions. Besides the thorax, we also simulated the performance of the dynamic bowtie in the abdomen and in the shoulders. All simulations were conducted in two dimensions and we ignore volumetric effects. In this simulation the photons were assumed to be monoenergetic at 60 keV. We did not model imperfections relating to the implementation of the dynamic bowtie, but assumed that we had direct access to the piecewise-linear attenuation profile that the embodiment of the invention should be able to furnish for us, subject only to the finite motor speed of the bowtie. All tests were compared to a reference bowtie similar to the body bowtie in a GE CT scanner.

The most basic task of the bowtie is to reduce the dynamic range on the detector. The dynamic range is defined as the largest possible ratio of photons arriving at any two measurements on the sinogram. The dynamic range with the traditional bowtie can be calculated simply by looking at the sinogram, by finding the ratio of the number of photons arriving at the least and most attenuated pixel in the sinogram.

To calculate the dynamic range with the dynamic bowtie, it was necessary to first determine the trajectories of the different wedges of the dynamic bowtie over time. To do this, we assumed that a pilot CT scan was available and solved an optimization problem whose objective was to minimize the dynamic range. For the purpose of this simulation, we assumed that the pilot CT scan was noiseless, although the addition of noise is not expected to change the results.

Minimizing the dynamic range was cast as a convex optimization problem so that the best trajectories could be calculated using the CVX convex optimization package with a guarantee on optimality. The object attenuation was measured by the pilot scan. The added bowtie attenuation on the other hand, was modeled by breaking up the bowtie into the component wedges in separate views. With M bowtie wedges and N views, the added bowtie attenuation was calculated as a linear combination of MN different images. To be precise, let $\theta$ be the continuous fan angle and $v$ be the discrete view number. Then we can define $$\mu_{tot}(\theta,v)=\mu_{object}(\theta,v)+\mu_{added}(\theta,v)$$

$$\mu_{added}(\theta,v)=\Sigma \chi_{ij} \Lambda(\theta-t) \delta(v-j)$$

The optimization problem was cast into the convex formulation $$\text{Minimize } \max(\mu_{tot}(\theta,v))-\min(\mu_{tot}(\theta,v))+\epsilon \Sigma x_{ij}^2$$

$$\text{Subject to } |x_{ij}-x_{(i+1)j}|<s_{max} \text{ for } i=1,2 \ldots M-1$$
$$0 \leq x_{ij} \leq x_{max}$$

Here, $\epsilon \Sigma x_{ij}^2$ is a regularization term with $\epsilon$ being a small positive constant. As defined, the dynamic range is unaffected by uniform shifts in attenuation, but adding on extra attenuation is undesired from a flux standpoint. $S_{max}$ is a constant which determines the highest speed by which the triangle functions can grow or shrink in time, and is set by the speeds of the motors and similar constraints.

In order to decrease the computational complexity, we ran the optimization problem on a downsampled sinogram with fewer views and angular samples. However, the optimal solution in the downsampled sinogram is expected to be quite good on the full sized version of the sinogram, as well.

As a reference, we compared the dynamic bowtie to a static bowtie. The bowtie used by the reference system is the GE body bowtie.

With the tube current modulation profile and the trajectories of the dynamic bowtie in hand, it was possible to determine both the radiation dose delivered and the noise statistics of the resulting scan. The variance of each pixel in the reconstruction was produced by adding the variance of each individual ray that is backprojected to a given pixel, scaled by a constant that depends on the deapodization kernel used. The variance of each ray, in turn, was found by assuming simple Poisson statistics at the detector.

The radiation dose was found using Monte Carlo simulations with the GEANT4 software package. To simplify the calculations, the original DICOM image was downsampled by a factor of four so that the simulations were run using only 128×128 pixels instead of the original 512×512 pixels. The two-dimensional picture was extruded by twenty centimeters in the third dimension in order to obtain an estimate of the dose contribution of photons that undergo Compton scattering. The bowtie itself was modeled as being purely attenuating, and photons that undergo Compton scattering from the bowtie itself are ignored. In interpreting the DICOM images, pixels less than −700 HU were regarded as air. Pixels between −700 and 200 HU were regarded as being composed of water of the density that would produce the observed HU value. Pixels above 200 HU were regarded as being a linear combination of cortical bone and water by volume, with the linear weights determined by the need to produce the observed HU value.

Beam Hardening Simulations

Using the same actuator trajectories previously obtained, a polychromatic (120 kVp) simulation of the bowtie was conducted to check that the beam hardening artifacts remained acceptable. The clinical data was segmented into air, cortical bone, and water. The images were then reconstructed in three ways: without any beam hardening corrections, with a beam hardening correction, and with a two-pass beam hardening correction. In order to more cleanly capture the effects of the beam hardening correction, we did not model the tissue as being mixtures of air, water and bone, but rather, segmented them in a hard, ternary fashion. This allowed the effects of beam hardening to be more clearly seen without any anatomical background. The beam hardening artifacts induced by the virtual bowtie were compared with those coming from a standard, static bowtie.

The two-pass beam hardening correction scheme was based on published two-pass algorithms. Briefly, in the first pass of the algorithm, the incident photon count was used in conjunction with the depth and material of the bowtie penetrated to estimate the equivalent water length. We applied filtered background projection (FBP) to this data to get a first pass image, which we then segmented into mixtures of water, bone, and air depending on CT number. In the second pass, we applied a forward projection step and estimated how much bone and water each ray would have passed through, and we used these numbers to estimate the magnitude of the error that was made in the first pass. The result was then applied as a correction term.

Results

Figure 3A:
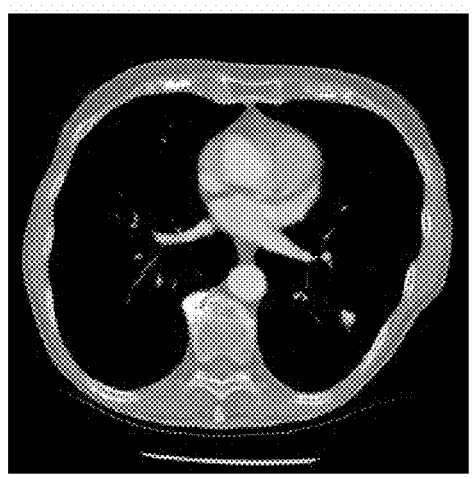
FIG. 3A is a starting DICOM image of a thorax for simulation.
Figure 3B:
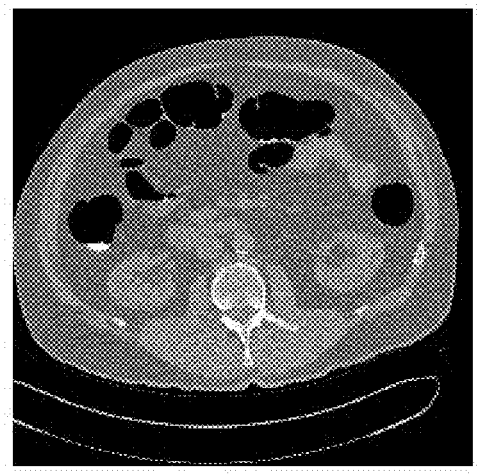
FIG. 3B is a starting DICOM image of an abdomen for simulation.
Figure 3C:
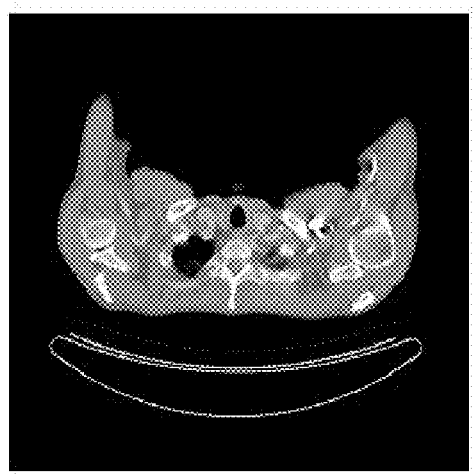
FIG. 3C is a starting DICOM image of shoulders for simulation.

A system of 17 actuators was assumed to produce the following images. FIGS. 3A-C show the three datasets that were used. FIG. 3A is a starting DICOM image of a thorax for simulation. FIG. 3B is a starting DICOM image of an abdomen for simulation. FIG. 3C is a starting DICOM image of shoulders for simulation.

Dynamic Range

Figure 4A:
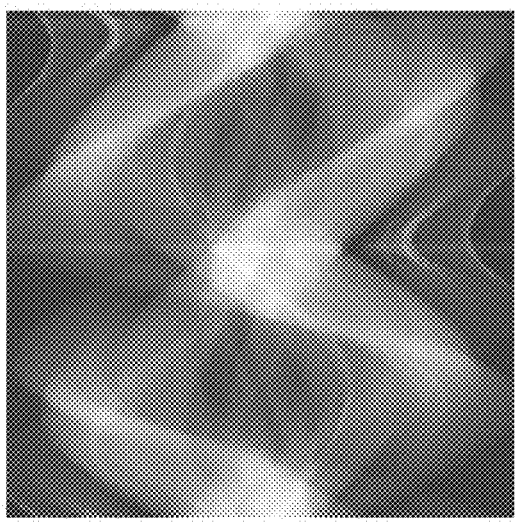
FIGS. 4A-F show an attenuation sinogram of shoulders, thorax, and abdomen.
Figure 4B:
Figure 4C:
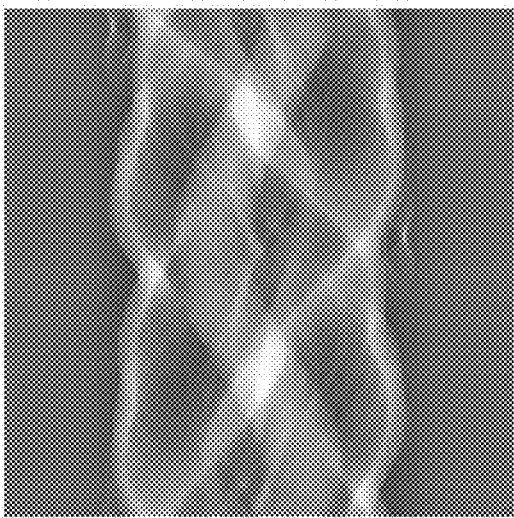
Figure 4D:
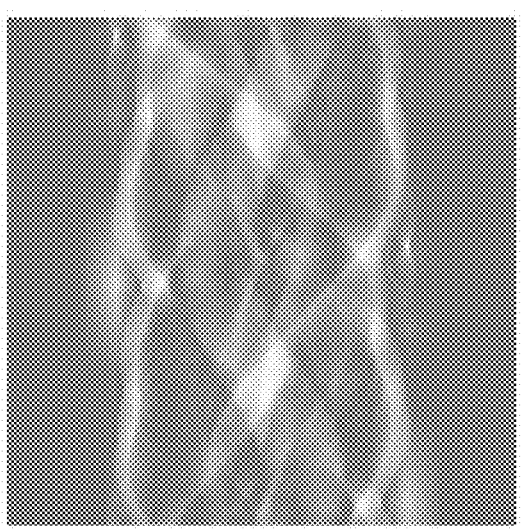
Figure 4E:
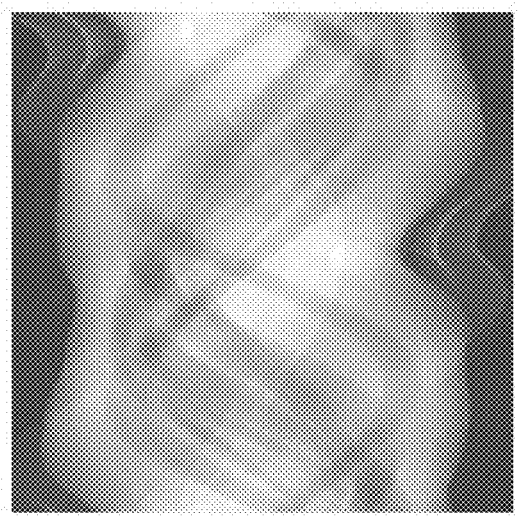
Figure 4F:
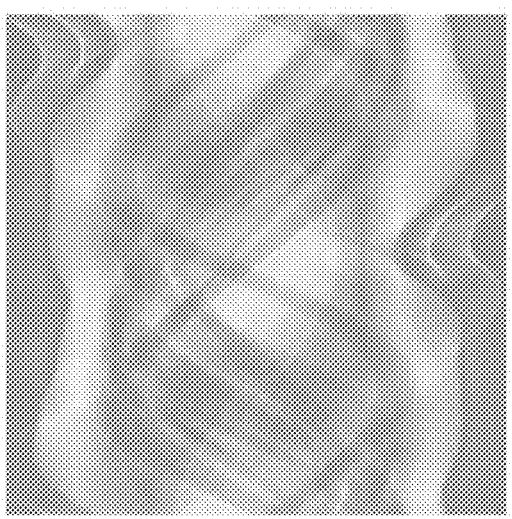

The dynamic range decreased by factors of four to fifty depending on the dataset used. FIGS. 4A-F show an attenuation sinogram of shoulders (FIGS. 4A-B), thorax (FIGS. 4C-D), and abdomen (FIGS. 4E-F). Results from the static bowtie are shown in FIGS. 4A, C, and E, and results from the dynamic bowtie are shown in FIGS. 4B, D, and F. The sinograms for the same dataset are shown at the same windowing. The dynamic range for the reference bowtie and for the embodiment of the dynamic bowtie is shown below.

| Dataset | Reference Bowtie Dynamic Range | Dynamic Bowtie Dynamic Range | Ratio |
| --- | --- | --- | --- |
| Adult thorax | 53 | 17 | 3.2x |
| Adult shoulder | 1577 | 133 | 11.9x |
| Adult abdomen | 381 | 14 | 27.1x |

Figure 5A:
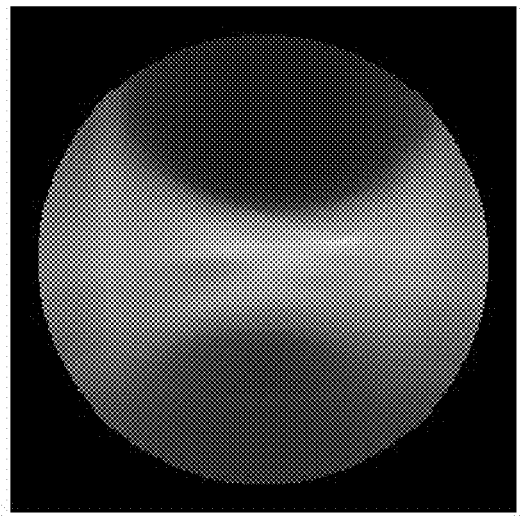
FIGS. 5A-F show the noise distribution, scaled by arbitrary reference noise of shoulders, thorax, and abdomen.
Figure 5B:
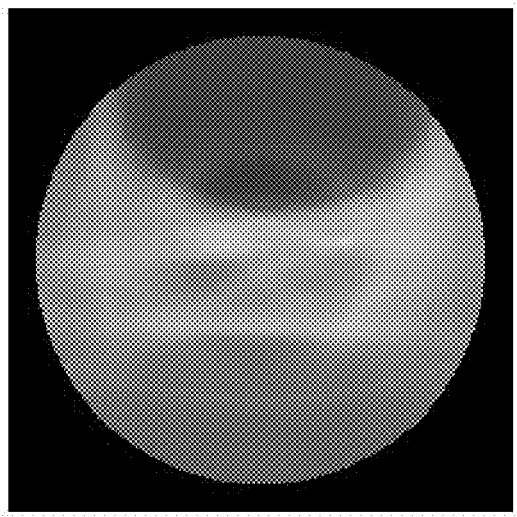
Figure 5C:
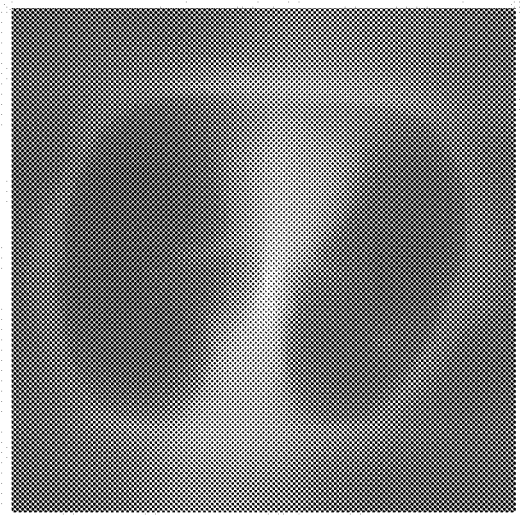
Figure 5D:
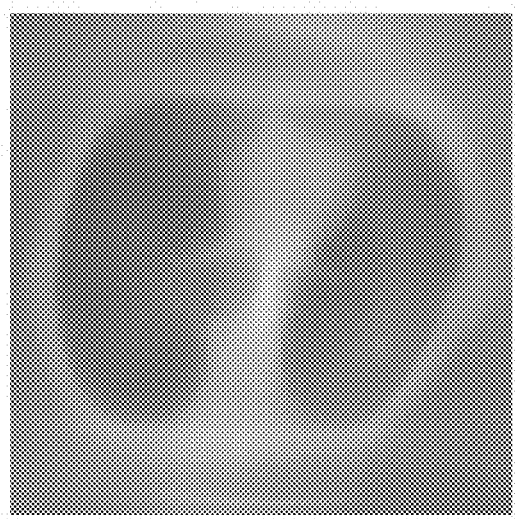
Figure 5E:
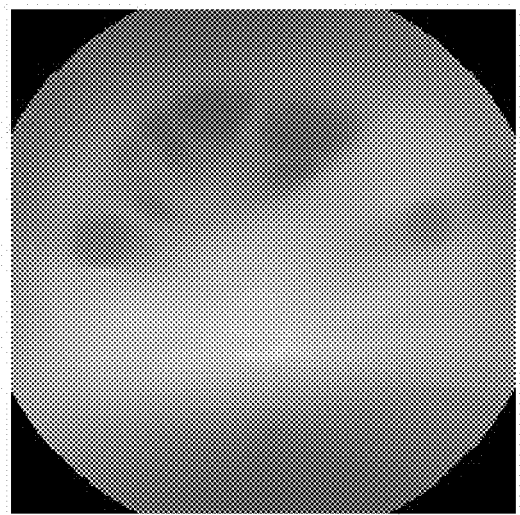
Figure 5F:
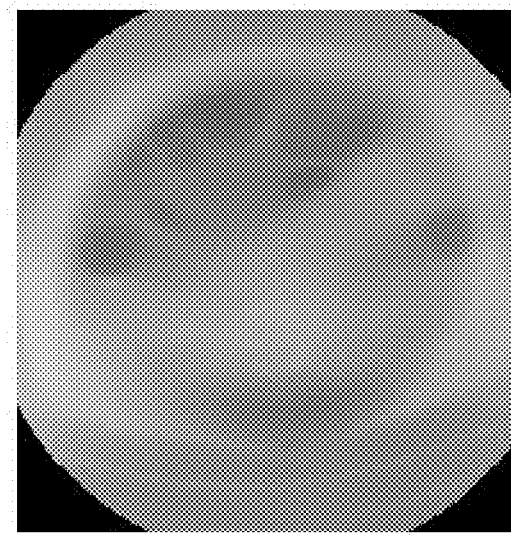

FIGS. 5A-F show the noise distribution, scaled by arbitrary reference noise of shoulders (FIGS. 5A-B), thorax (FIGS. 5C-D), and abdomen (FIGS. 5E-F). The noise distribution is reported as standard deviation of pixel value and not a variance. FIGS. 5A, C, and E show the scaled noise distribution for a reference bowtie. FIGS. 5B, D, and F show scaled noise distribution for a dynamic bowtie.

Figure 6A:
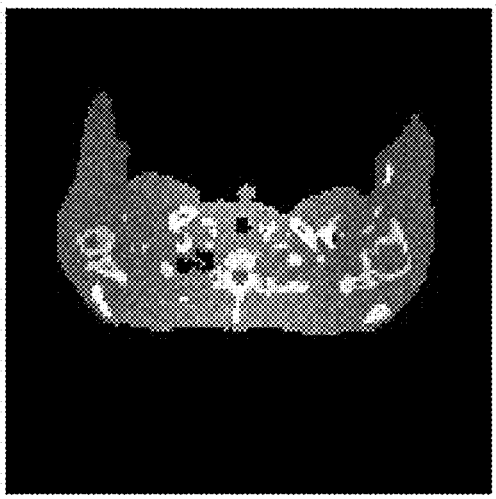
FIGS. 6A-F show the dose distribution as calculated from Monte Carlo simulation.
Figure 6B:
Figure 6C:
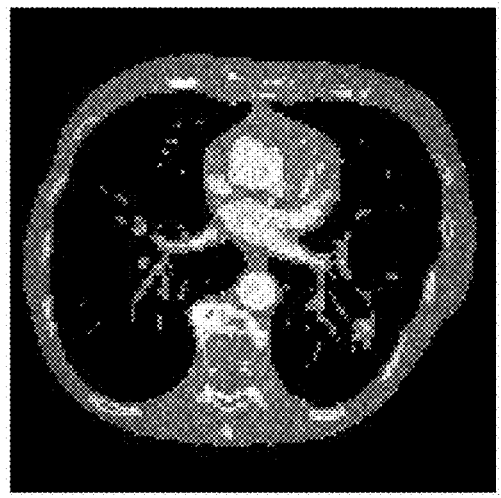
Figure 6D:
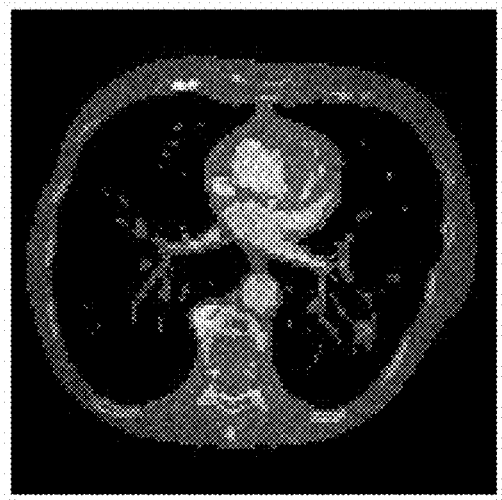
Figure 6E:
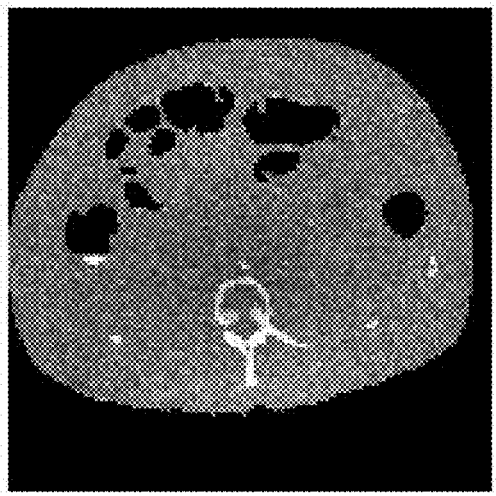
Figure 6F:
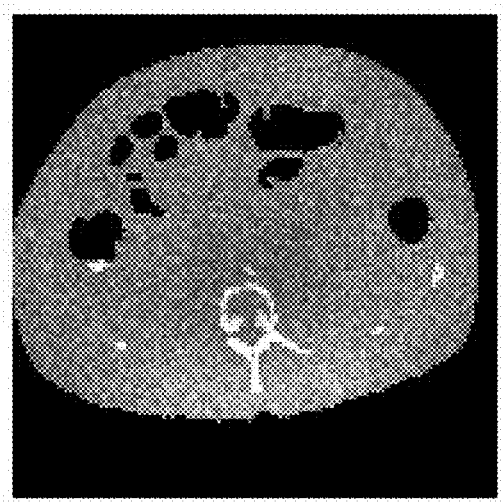

FIGS. 6A-F show the dose distribution as calculated from Monte Carlo simulation. FIGS. 6A, C, and E are simulations that result from a dynamic bowtie. FIGS. 6B, D, and F are simulations that result from using a static bowtie filter.

A marked decrease in dose can be observed in some datasets, e.g. in the shoulder (FIG. 6A-B). If desired, the optimization objective could have been set to minimize a noise metric such as peak or average variance for a fixed level of dose.

Beam Hardening Simulations

Figure 7A:
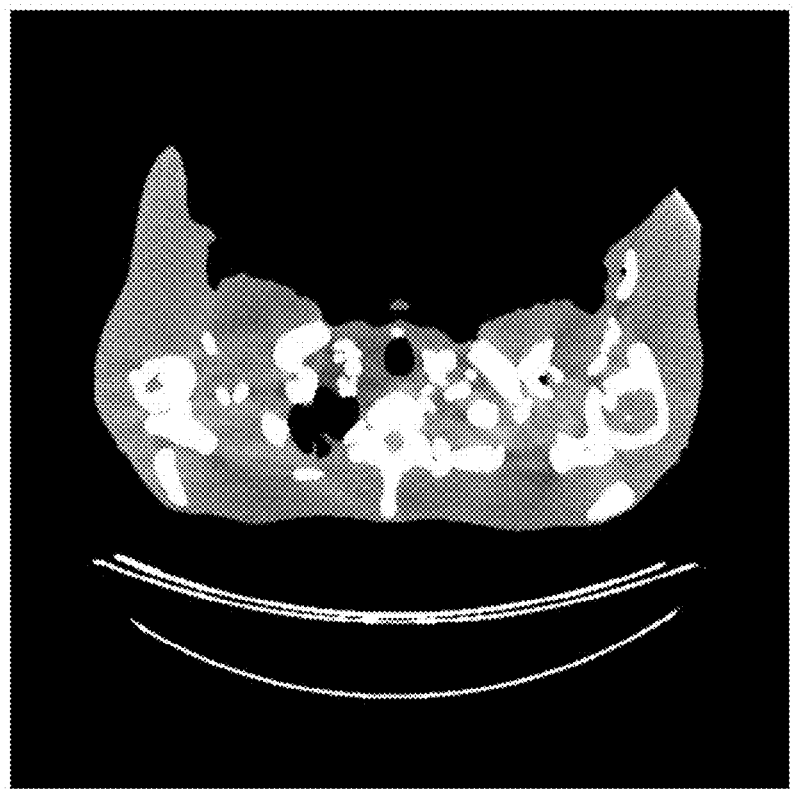
FIG. 7A shows the result of a hardening correction using a single pass algorithm.
Figure 7B:
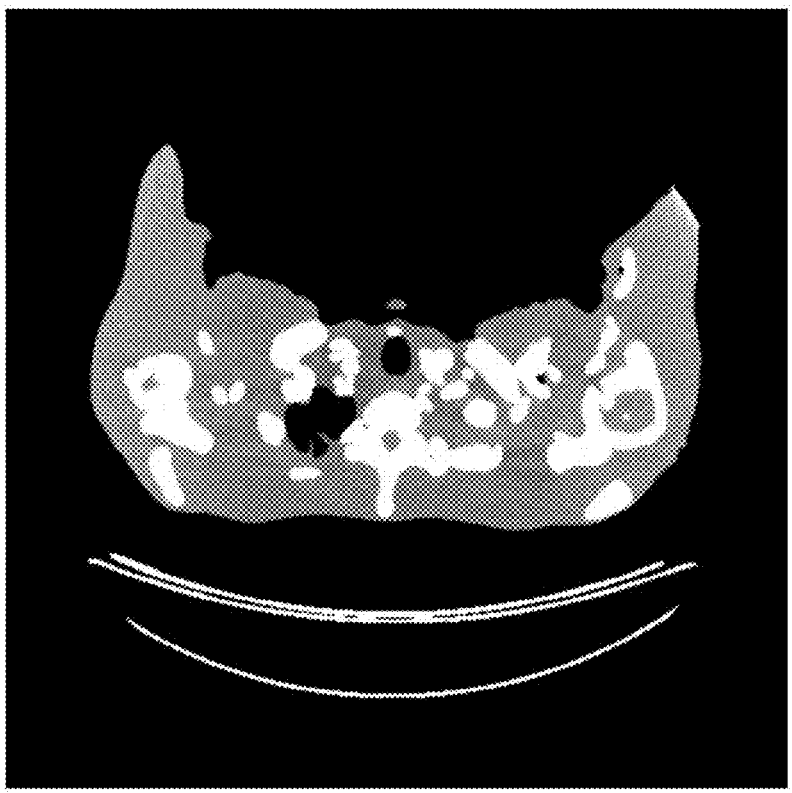
FIG. 7B shows the result of a hardening correction using a two-pass algorithm.

A simple shoulder phantom was segmented in a hard ternary fashion into cortical bone, water, and air. The initial reconstruction with only a one-pass correction resulted in some residual beam hardening artifacts. The one-pass correction is a water beam hardening correction that is channel and view-dependent, compensating for the different lengths of bowtie attenuation. A two-pass algorithm was effectively able to clean it up. FIG. 7A shows the result of a hardening correction using a single pass algorithm. FIG. 7B shows the result of a hardening correction using a two-pass algorithm. The artifact level of each was comparable to the counterpart standard bowtie image.

The two-pass algorithm first applies the original one-pass correction, which is a view and channel dependent water beam hardening correction. Then, the amount of bone present in each ray is estimated by segmentation and forward projection. This amount of bone is used to estimate the error present in the water beam hardening correction, and the estimated error is then subtracted from the image.

Based on the mathematical starting point of producing piecewise linear functions using triangle functions, an embodiment of the invention provides a dynamic bowtie that can be implemented using wedges, with different axial slices of the wedge resulting in triangles of different heights. This dynamic bowtie design remains quite practical and actionable.

In simulations, the dynamic bowtie was able to reduce the dynamic range by factors from between 4 to 50 depending on the part of the body studied. These results suggest that the possibility of using this dynamic bowtie in conjunction with photon-counting detectors of relatively modest count rates. The dynamic bowtie could also be applied to other objectives, such as noise or dose reduction. The thorax image was challenging because of the sharp transitions between the lungs and the tissue surrounding the lungs, but reasonably good results were still obtained, and here the dynamic bowtie had the fringe benefit of reducing the radiation dose delivered without increasing the maximum noise of the image. In the shoulders and in the abdomen, the dynamic range was reduced by over an order of magnitude. The beam hardening artifacts of the dynamic bowtie were also studied, and preliminary results suggest that while they are somewhat different from traditional beam hardening artifacts, they can be corrected with a two-pass algorithm.

EXAMPLES

Figure 8:
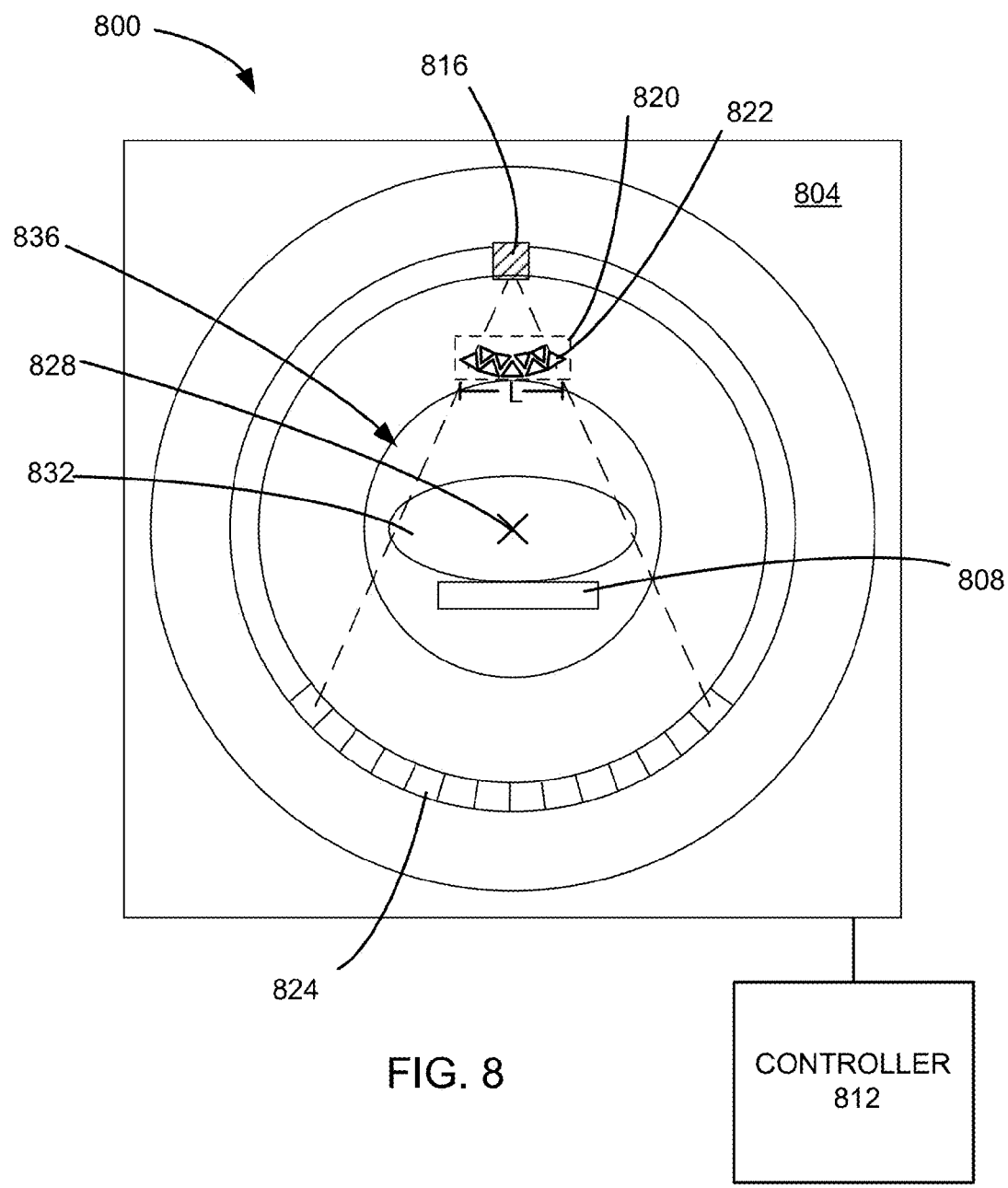
FIG. 8 is a schematic end view of an x-ray CT system that may be used in an embodiment of the invention.

To facilitate understanding of the invention, FIG. 8 is a schematic end view of an x-ray CT system 800 that may be used in an embodiment of the invention. The CT system comprises a gantry 804, a support 808, a dynamic bowtie filter 820, and a controller 812. The dynamic bowtie filter 820 is like the dynamic bowtie filter shown in FIG. 2A and FIG. 2B and comprises a plurality of wedges 822. The gantry supports an x-ray source 816, a dynamic bowtie filter 820, and an x-ray detector 824. The gantry 804 rotates the x-ray source 816, dynamic bowtie filter 820, and x-ray detector 824 around an axis of rotation 828 that extends into the page. The support 808 supports an object 832 to be scanned. The support 808 or gantry 804 translates the object 832 with respect to the x-ray source 816, dynamic bowtie filter 820, and x-ray detector 824 along the axis of rotation 828 through an aperture 836 in the gantry 804. In this embodiment, the x-ray source 816 provides a collimated beam that has a cross-section with a length (L) and thickness. The axis of rotation 828 is substantially perpendicular to the length of the cross-section of the collimated beam.

The dynamic bowtie filter 820 is shown in FIG. 8 and also in FIGS. 2A and 2B. It can be seen that along the direction of the length L of the cross-section of the x-ray beam the thicknesses of the wedges 822 change. More specifically, since the wedges are triangular, the thicknesses of the wedges increase and then decrease or alternately increase and decrease along the direction of the length L of the cross-section. In this embodiment, the wedges are provided in a first row 204 and a second row 208, as shown in FIG. 2B. The wedges in the second row are placed to overlap with wedges in the first row, so that thicker parts of the wedges in the second row line up with the junctions between wedges in the first row and thicker parts of the wedges in the first row line up with the junctions between wedges in the second row along the direction between the x-ray source and the object. In this embodiment, the backsides 212 of the wedges forms a curved rectangular surface, as shown in FIG. 2A.

Figure 9:
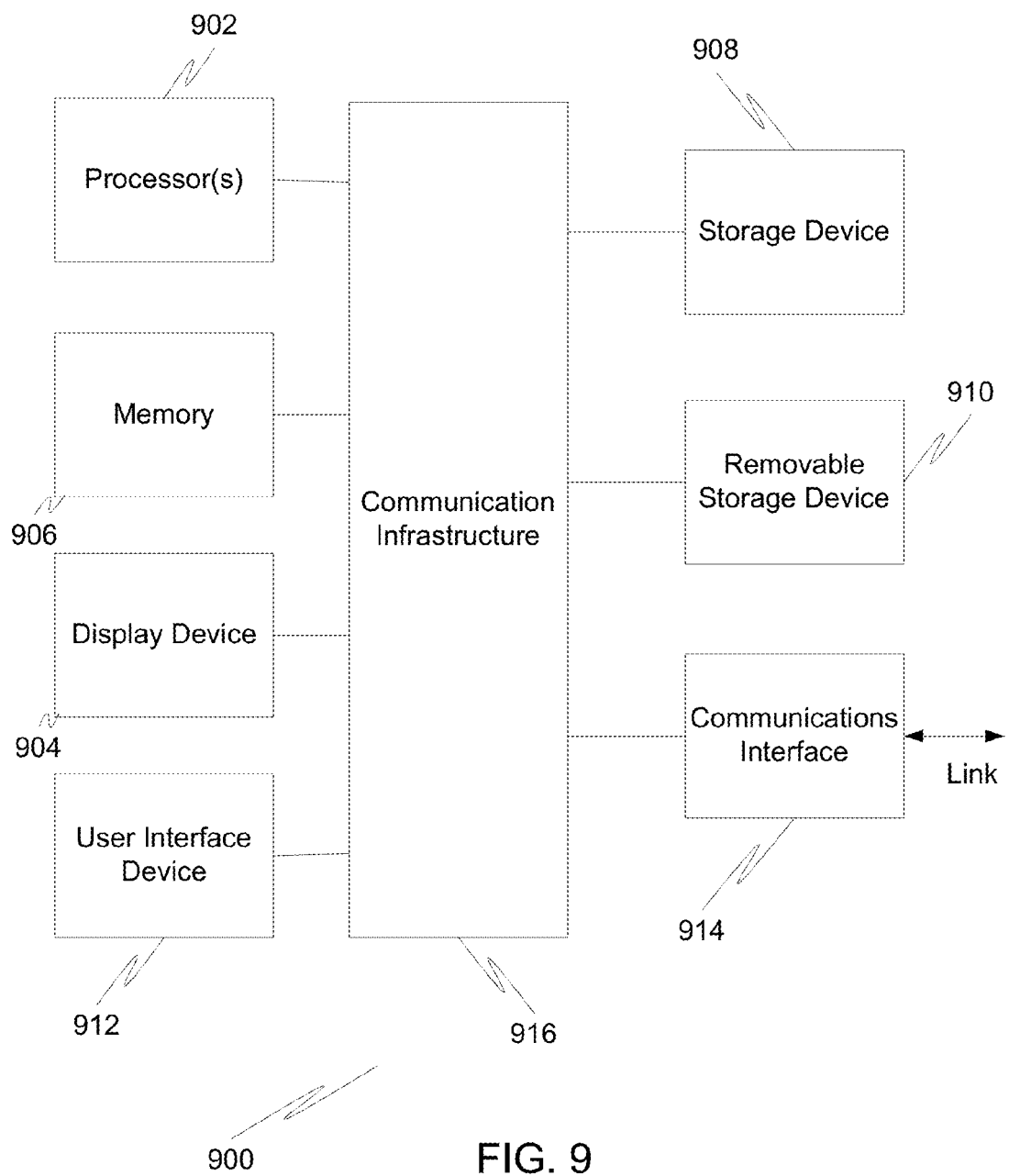
FIG. 9 is a high level block diagram showing a computer system, which is suitable for implementing a controller used in embodiments of the present invention.

FIG. 9 is a high level block diagram showing a computer system 900, which is suitable for implementing a controller 812 used in embodiments of the present invention. The computer system may have many physical forms ranging from an integrated circuit, a printed circuit board, and a small handheld device up to a huge super computer. The computer system 900 includes one or more processors 902, and further can include an electronic display device 904 (for displaying graphics, text, and other data), a main memory 906 (e.g., random access memory (RAM)), storage device 908 (e.g., hard disk drive), removable storage device 910 (e.g., optical disk drive), user interface devices 912 (e.g., keyboards, touch screens, keypads, mice or other pointing devices, etc.), and a communication interface 914 (e.g., wireless network interface). The communication interface 914 allows software and data to be transferred between the computer system 900 and external devices via a link. The system may also include a communications infrastructure 916 (e.g., a communications bus, cross-over bar, or network) to which the aforementioned devices/modules are connected.

Figure 10:
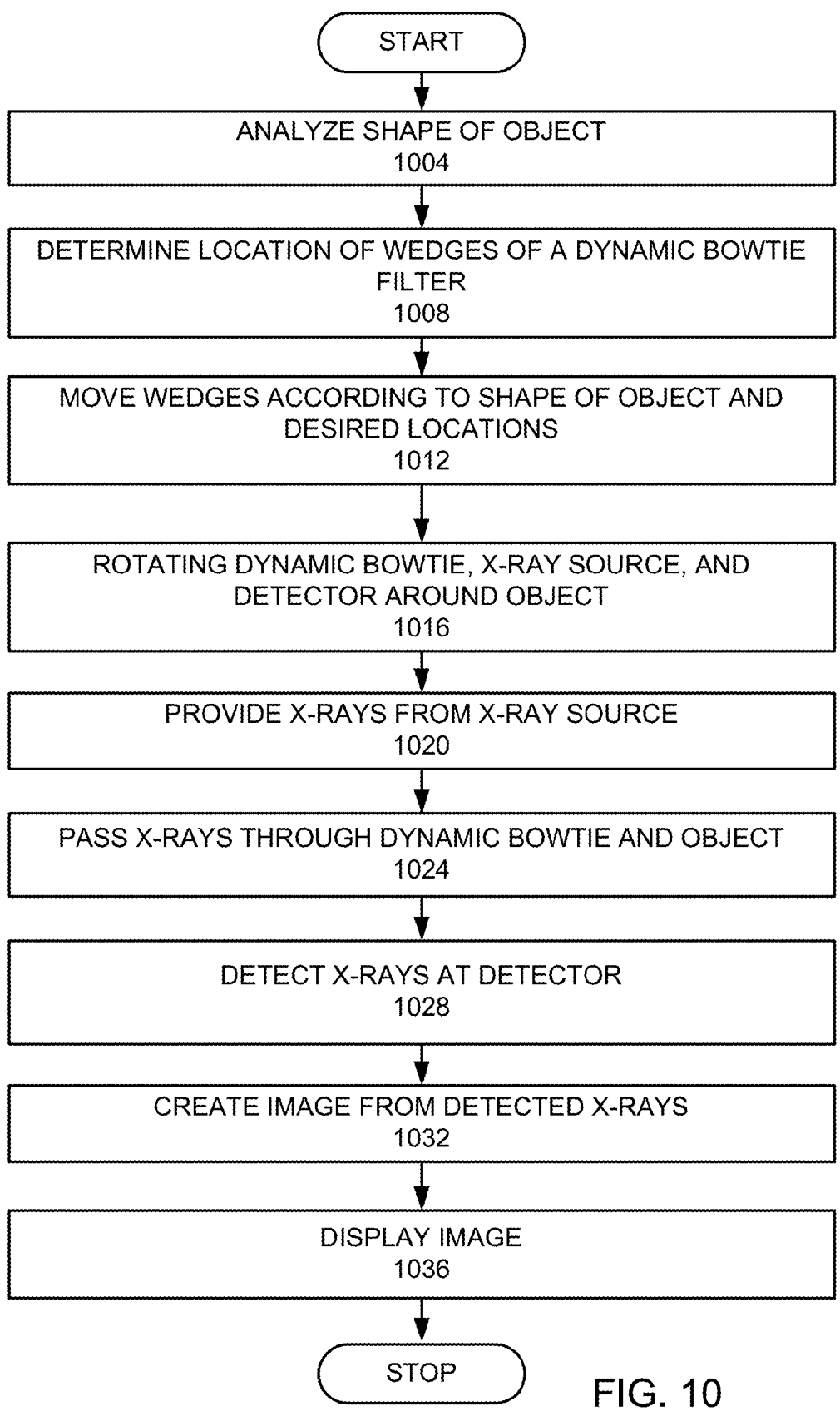
FIG. 10 is a high level flow chart of an embodiment of the invention.

To facilitate the understanding of the invention, FIG. 10 is a high level flow chart of an embodiment of the invention. An object 832 is placed on the support 808, which translates the object along the axis of rotation 828 into the aperture 836 of the gantry 804. The object's shape is analyzed (step 1004). The location of the wedges 822 of the dynamic bowtie filter 820 as a function of time in the scan is determined (step 1008). The wedges 822 begin to move according to the shape of the object 832 and the desired wedge locations over time (step 1012). The x-ray source 816, dynamic bowtie filter 820, and x-ray detector 824 are rotated around the axis of rotation 828 (step 1016). The x-ray source 816 provides x-rays (step 1020). The x-rays are passed through the dynamic bowtie filter 820 (as it changes over time) and object 832 (step 1024) while the gantry rotates. The x-rays are detected at the detector (step 1028). An image is created from the detected x-rays (step 1032). The image is displayed (step 1036).

Figure 11:
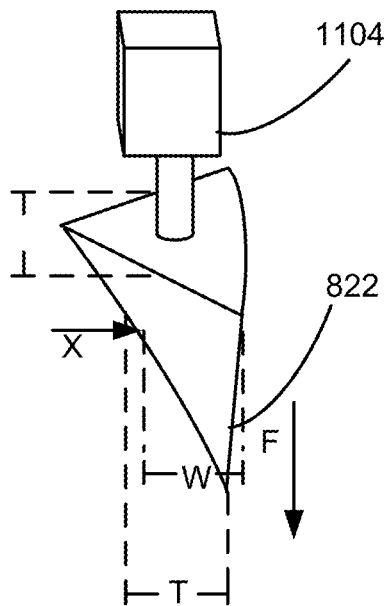
FIG. 11 is a schematic perspective view of a wedge attached to an actuator.

FIG. 11 is a schematic perspective view of a wedge 822 attached to an actuator 1104. In this embodiment the actuator 1104 moves the wedge 822 in a direction perpendicular to the length of the cross-section collimated x-ray beam. In this embodiment, since the direction perpendicular to the length of the cross-section of the x-ray is parallel or substantially parallel to the axis of rotation 828 and the movement of the support 808, the actuator 1104 moves the wedge 822 parallel or substantially parallel to the axis of rotation 828 and the movement of the support 808. The wedges 822 increase or decrease in thickness along the direction of the movement by the actuators 1104. The movement by the actuator 1104 increases or decreases the cross-section of the wedge 822 through which the fan shape x-ray passes, thus dynamically changing the bowtie filter shape. In this embodiment, a first direction F is a direction of movement by the actuator that is away from the actuator. The thickness T of the wedge decrease along the first direction. In addition, a direction X is along a path from the x-ray source to the object. The width of the wedge W as seen by the x-ray beam at location X increases as the wedge is moved in the direction of the arrow. As shown in FIG. 2A, the thicknesses of the wedges in the first and second row decrease in the first direction.

Additional Embodiments

Location Measurement

An embodiment of the invention focused on the use of the dynamic bowtie to enable photon counting detectors. However, another embodiment may use traditional energy-integrating detectors and the dynamic bowtie to control radiation dose. The fundamental ability granted by the dynamic bowtie is to customize the distribution of radiation to the imaging task, and the addition of the dynamic bowtie would enable region-of-interest scans and would allow CT scanners to reduce the radiation to sensitive organs. Prior experiments with the virtual dynamic bowtie, relevant to inverse geometry systems, suggest that the magnitude of this dose efficiency improvement can be quite large. Other embodiments of the invention may provide increased or decreased complexity of the bowtie design, by adding more actuators or faster motors. Other embodiments of the invention are designed for controlling variations in the z-direction or to reduce the detected scatter-to-primary ratio. An actuator may drive many wedges or each wedge may have its own actuator.

In some cases, only imaging of a known fraction of the cross-section of the object may be needed. For example, when imaging the heart, the image quality in other parts of the cross-section may not need to be high while it may be desirable to reduce the radiation dose to those other regions (e.g., the breast). In such cases, the dynamic bowtie can be used to substantially reduce the x-ray flux in rays that do not pass through the needed portions and thereby protect the other parts from radiation.

As mentioned above, it is important that the location of the wedges be known; otherwise the dynamic bowtie may produce artifacts. The lack of precision in the actuator may result in error in the amount of attenuation produced by the dynamic attenuation profile, and this error will propagate into the reconstruction. A real-time sensing method can eliminate this source of error.

Figure 12:
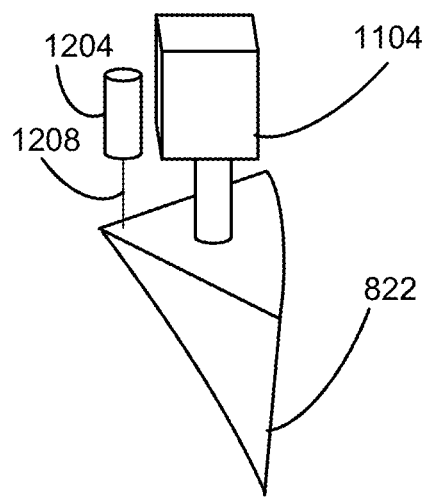
FIG. 12 schematic perspective view of a wedge and actuator with an optical system.
Figure 13:
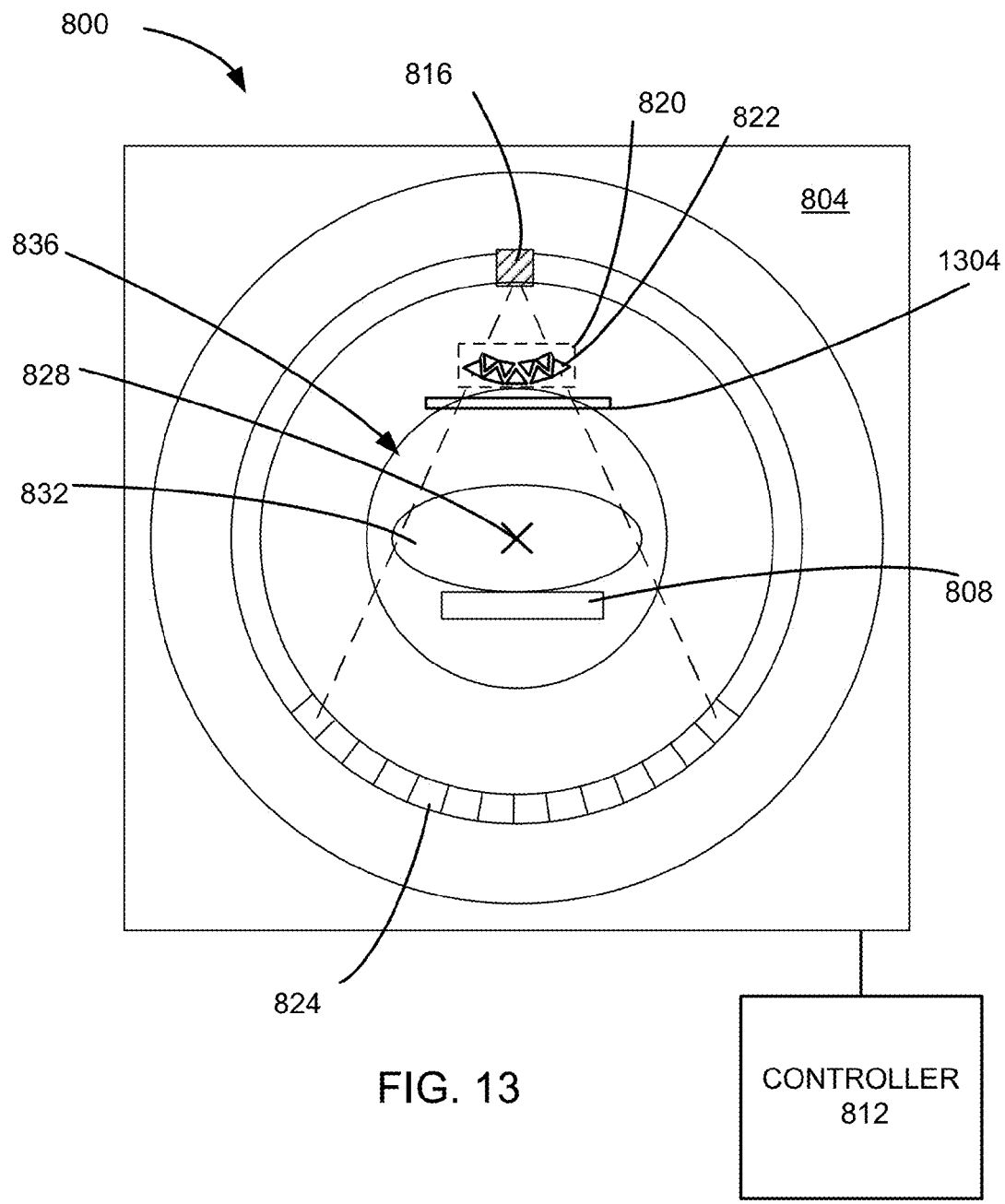
FIG. 13 is a schematic end view of a CT system comprising a gantry, a support, a dynamic bowtie filter, a controller, and a thin detector.

In some embodiments of the invention, calibrating the dynamic bowtie is provided by determining, with great precision, the location of the individual wedges of the bowtie and the provided attenuation profile. In one embodiment, actuators provide a very high level of precision. In another embodiment, location systems, such as an optical tracking system, are used to determine the location of the wedges. FIG. 12 schematic perspective view of a wedge 822 and actuator 1104. An optical system 1204, such as an interferometer is used to accurately measure the location of the wedge 822 by reflecting a beam of light 1208 on the wedge 822. In another embodiment, a thin detector could be used to determine the pre-patient attenuation profile. A "thin detector," is a detector placed between the dynamic bowtie and the patient, which would absorb and detect only a small fraction of the photons that pass through it, allowing most of the flux to be used on the patient. The thin detector would then provide a direct measure of the flux profile that is incident on the patient. FIG. 13 is a schematic end view of a CT system comprising a gantry 804, a support 808, a dynamic bowtie filter 820, a controller 812, and a thin detector 1304. In one embodiment, only a single line of detectors (rather than an area detector) could be used. In such an embodiment, the detector could be displaced off-center, into a region that would otherwise be collimated, and then the detector could be made thick (that is, absorb more of the photons incident on it) because they would be collimated anyway. With the thick line detector, the flux profile everywhere else would be inferred rather than directly measured. The optical tracking system would likewise determine the location of the wedges, and the flux profile would then be inferred from the wedge locations.

Figure 14:
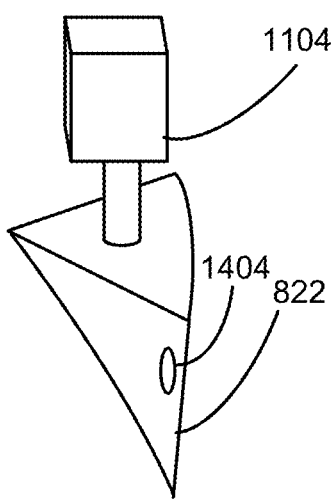
FIG. 14 is a schematic view of a wedge with an actuator and a high contrast marker.

Because the entire x-ray source assembly is subject to mechanical instabilities, it is important to determine the locations of the wedges as perceived by the detector. Neither the thin detector nor the optical tracking system can provide such "absolute locations," meaning the locations as perceived by the detector. They provide only relative locations, meaning that in the presence of mechanical instabilities (such as a slight rotation of the bowtie or source assembly), they cannot provide an accurate depiction of the flux profile on the detector. To resolve the absolute locations of the wedges, another embodiment of the invention uses high-contrast markers. These high-contrast markers could be, for example, small beads of an appropriately attenuating metal (for example, tungsten) that are embedded within the wedges at known positions. These beads will cast a shadow on the detector, and the locations of the shadows would be used to determine the position of the wedges. The high-contrast markers could modestly degrade the quality of the data that lie in the shadow of the marker, so as one option, the high-contrast markers could only be used on the outermost wedges, so that the shadows of the high-contrast markers would usually not overlap with the shadow of the patient (unless the patient is large). Once the high-contrast markers have been used to provide the location of some of the wedges, the relative position could then be determined by an optical tracking system or any other concept thus far described. FIG. 14 is a schematic view of a wedge 822 with an actuator 1104 and a high contrast marker 1404.

Wedge Design for a Smooth (Continuous in Derivative) Attenuation Profile

The sharp corners in the dynamic piecewise-linear attenuation profile may also cause errors because of interactions with focal spot drift. By "sharp corners," we mean that the derivative in the piecewise-linear profile is discontinuous. Some embodiments of the invention alleviate these artifacts and real-world imperfections.

The piecewise-linear attenuation profile in previously described embodiments of the invention has the advantage of being continuous. This continuity will reduce some immediate artifacts, such as those resulting from the nonzero focal spot size. However, the piecewise-linear attenuation profile is discontinuous in its derivative, which may cause problems when the system is subject to focal spot drift or motion.

Other embodiments have alternative wedge shapes which are not discontinuous in the derivative or which may have other advantages. Fundamentally, the wedge shapes only need to form a mathematical basis for the functions to be used in an embodiment. Other embodiment may use more complicated splines, or the function could be piecewise-quadratic rather than piecewise-linear.

Figure 15:
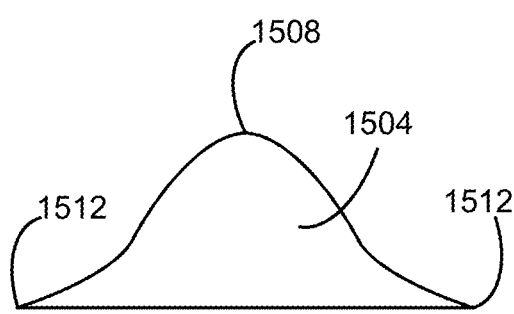
FIG. 15 is a top view of a wedge that has a more Gaussian shape.

In an embodiment of the invention, wedge designs produce an attenuation profile that is close to piecewise-linear, but do not suffer from the derivative-discontinuous transitions. One embodiment is to smooth the triangular cross-sections by convolving them with a smoothing function such as a Gaussian. Another embodiment is to round the corners of the triangle or to modify them in such a way that the resulting attenuation profile becomes continuous in the derivative. FIG. 15 is a top view of a wedge 1504 that has a more Gaussian shape. The central corner 1508 is rounded. The sides near the outer corners 1512 are curved to provide a more Gaussian shape.

In other embodiments different wedge shapes are possible that are not limited to an attenuation profile that is piecewise-linear. Piecewise-linearity has the advantage of being simple, and some of the above embodiments provide a variation of our previously described piecewise-linear design which would produce similar attenuation profiles but be continuous in the derivative.

In an embodiment of the invention, the actuators move the wedges as the actuators and wedges are rotated around the object. In one embodiment, the movement by the actuators during rotation accommodates the rotational position of the x-ray source and dynamic bowtie filter with respect to the object. In one embodiment, the movement is preprogrammed in relation to the rotational position based on data acquired from the object or on prior knowledge or assumed shape of the object. In another embodiment, an analysis of the object and measured by the actual measured projections governs in real time how the wedges are actuated during rotation.

In one embodiment, the dynamic movement, actuation of the wedges during rotation, is for evening out noise. In another embodiment, the dynamic movement is for imaging one or more specific areas of interest, while ignoring other areas.

One of the critical challenges with the dynamic attenuator is the question of calibration. The locations of the wedges must be quite precisely known so that the radiation exposure profile incident on the patient can be estimated. Other embodiments provide additional methods for detecting the location of the wedges.

FIG. 16 is a schematic view of a wedge 822 with an actuator 1104 used in another embodiment. In this embodiment, a series of markings (such as dots) 1604 are placed on each wedge 822, and an optical sensor 1608, such as a camera, is placed used to detect the location of each of the markings 1604. The location of each mark could then be calibrated to the location of each wedge. The resolution of this method is dependent on the resolution of the optical sensor, but a much higher sensitivity is provided by using multiple markings 1604 on each wedge 822. The locations of the series of markings 1604 may be converted using the calibration data to a location of the wedge. An average can be used to reduce noise. In other embodiments, the optical sensor 1608 is a 1D sensor array, which may be preferred for its high speed and low cost. If the optical sensor 1608 is a 1D sensor array, the series of marking 1604 would be a striped pattern which would indicate the wedge's location.

FIG. 17 is a schematic view of a wedge 822 with an actuator 1104 used in another embodiment. A light source system 1704, such as a laser system or more generally some form of structured light creates a light beam 1706, which creates a light spot 1708 on the wedge 822. An optical sensor 1712 detects to location of the light spot 1708. For example, a laser dot could be used to triangulate the position of the wedge, in an "active stereo" setup. To create a light spot 1708 on a plurality of wedges, the light source system 1704 in one embodiment would provide a plurality of lasers, where each wedge has a corresponding laser. In another embodiment, a single laser may create a plurality of light beams to illuminate a plurality of wedges.

FIG. 18 is a schematic view of a wedge 822 with an actuator 1104 used in another embodiment. A linear scale 1804 is placed on a shaft 1806 extending from the actuator 1104 to the wedge 822. A linear encoder 1808 is placed in a position so that the linear encoder 1808 is able to sense the linear scale 1804. In this embodiment, the linear encoder 1808 is an optical linear encoder. The linear scale 1804 is an optical encoder pattern. In other embodiments a magnetic linear encoder is used with a magnetic linear scale. In other embodiments, the linear scale is attached directly to the wedge. A magnetic sensor array could similarly be used.

In an embodiment each wedge may have an optical sensor, so that a plurality of wedges has a plurality of optical sensors, wherein the plurality of optical sensors forms an optical sensor system.

Figure 19:
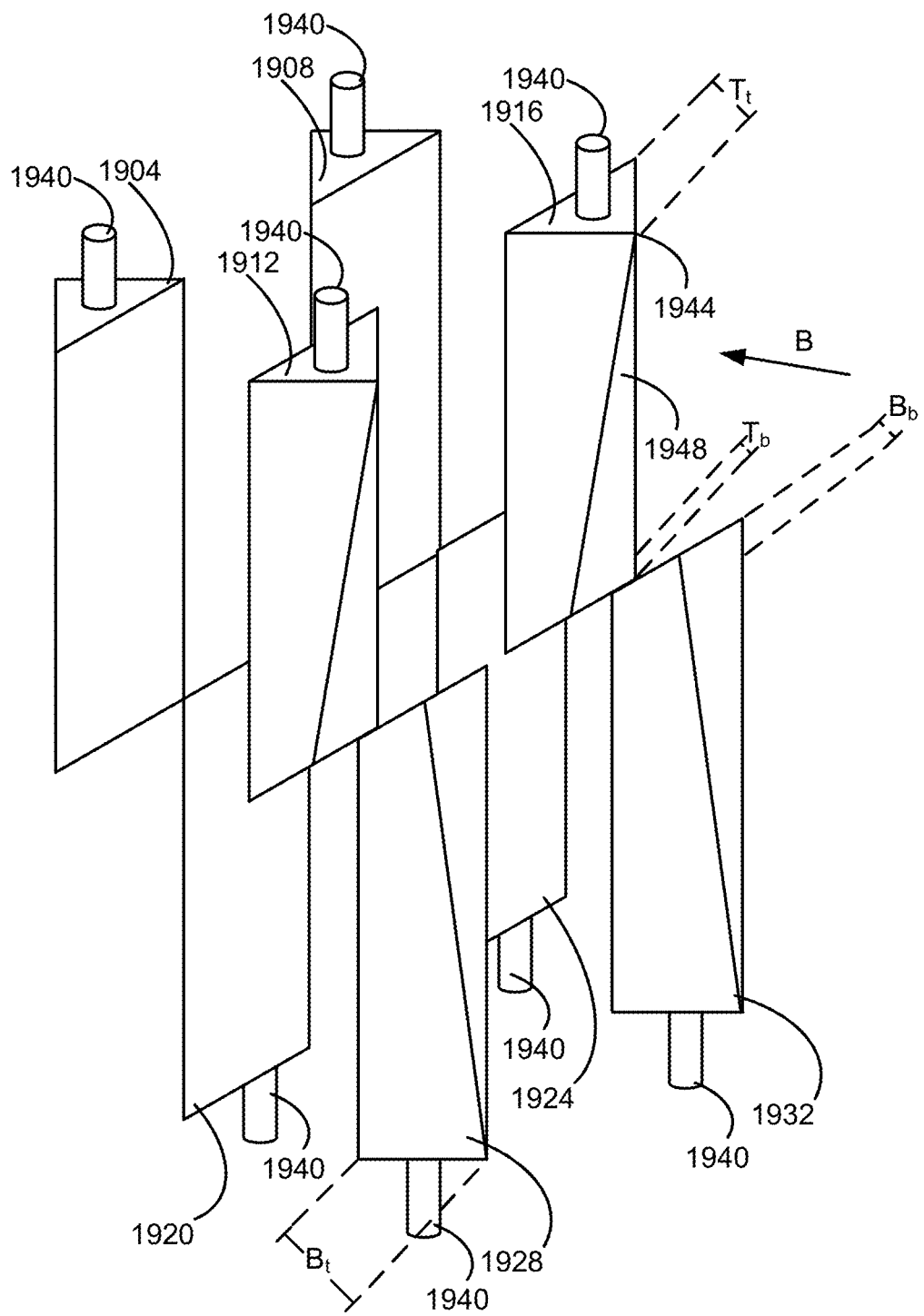
FIG. 19 is a perspective view of another embodiment of the invention.

FIG. 19 is a perspective view of another embodiment of the invention. In this embodiment there is a first wedge 1904, an second wedge 1908, a third wedge 1912, a fourth wedge 1916, a fifth wedge 1920, a sixth wedge 1924, a seventh wedge 1928, and an eighth wedge 1932. All of the wedges have a length lying along a z direction, positive z direction is defined as upward. The first, second, third, and fourth wedges 1904, 1908, 1912, 1916 form an upper plane of wedges. The fifth, sixth, seventh, and eighth wedges 1920, 1924, 1928, 1932 form a lower plane of wedges. The first, second, third, and fourth wedges 1904, 1908, 1912, 1916 in the upper plane of wedges have a triangular cross section at the top, where a corner 1944 of the triangular cross section is reduced along a negative z direction, so that the thickness at the top $T_t$ is greater than the thickness at the bottom $T_b$. In this embodiment, the reduction of the corner 1944 forms a reduction plane 1948. In this embodiment, the first, second, third, and fourth wedges 1904, 1908, 1912, 1916 have actuators 1940 connect at their tops that provide movement in the z direction. The fifth, sixth, seventh, and eighth wedges 1920, 1924, 1928, 1932 form a lower plane of wedges have a triangular cross section at the bottom, where a corner of the triangular cross section is reduced along a positive z direction, so that the thickness at the top $B_t$ is less than the thickness at the bottom $B_b$. In this embodiment, the fifth, sixth, seventh, and eighth wedges 1920, 1924, 1928, 1932 have actuators 1940 connect at their bottoms that provide movement in the z direction. As a result, the upper plane of wedges have a thickness that increases in the positive z direction, which is a direction of movement and the lower plane of wedges have a thickness that decreases along the positive z direction of movement.

In another embodiment, the physical thickness of the wedges does not change in the z direction; however, the x-ray equivalent thickness does change. This can be produced, for example, by encasing a metallic wedge in a plastic core that is largely transparent to x-rays. This is understood to be essentially equivalent to the described invention. With this design, it may be that the upper plane of wedges have a thickness which decreases in the positive z direction, or that the lower plane of wedges have a thickness which increase in the positive z direction.

The first and second wedges 1904, 1908 make a first row of wedges that overlap with a second row of wedges formed by the third and fourth wedges 1912, 1916. This overlapping of rows is described in previous embodiments. In this embodiment the fifth and sixth wedges 1920, 1924 are in the first row and the seventh and eighth wedges 1928, 1932 are in the second row, where the fifth and sixth wedges 1920, 1924 overlap with the seventh and eighth wedges 1928, 1932.

An x-ray beam passes through the direction designated as B. The triangular cross-section of the wedges causes a change in wedge thickness along the length of the cross-section of the collimated x-ray beam. The overlapping wedges cause the thickness of the wedges to alternately increase and decrease along the length of the cross-section of the collimated x-ray beam.

In an example, if a compensator is provided with a minimum attenuation of 0.5 mm of iron, this would require about an 80% increase in tube power, which is significant. If the compensator is removed, and instead the above wedges are used only a 40% increase in tube power is required. The noise of the data in reconstruction will become nonuniform, because some of the rays are attenuated by more or less attenuation. The rays that have fewer photons will have reduced signal to noise ratio (SNR) and a dose efficient reconstruction could downweight these rays appropriately and upweight rays with higher SNR, which is addressed in the reconstruction algorithm.

Other embodiments may have more than two rows such as three or four rows.

It is known that the use of k-edge filters can improve dose efficiency of spectral imaging. K-edge filters show increased attenuation past the k-edge and an appropriate length of k-edge filter can separate one broad spectrum into effectively two narrow spectra. Meanwhile, the dynamic attenuator that we have proposed creates a thickness piecewise-linear in fan angle and is ideal for use in photon-counting x-ray detectors (PCXDs) which require control of the incident flux in order to prevent pulse pile-up. These PCXDs are capable of spectral imaging and would especially benefit from k-edge filtration. One drawback of the k-edge filtration is that it reduces the amount of flux available to the system.

In another embodiment, the k-edge material is used for some or all of the wedges in a dynamic attenuator. One example is gadolinium, although elements with atomic numbers somewhat lower or higher than gadolinium would be appropriate. The exact filter material could be a compound of gadolinium, and could be alloyed with other materials in order to decrease its concentration and to ease the manufacturing process. Some or all of the attenuating wedge elements would be composed of this k-edge material. There are several advantages to this. The dynamic attenuator and PCXD already have synergistic effects, and using a k-edge filter could help even more. The use of conventional materials, such as iron, would harden the beam and could harm the spectral resolving capabilities from the PCXD system because the number of high-contrast low energy photons would be reduced. The K-edge material could provide an equivalent amount of attenuation, but maintain some low energy photons. Instead, the middle energy photons, which can be thought of as providing the least amount of information for the basis material decomposition, would be removed. Additionally, the amount of k-edge filtration would be easily tuned, and further, the attenuation would scale naturally where the system could afford it. For example, in rays where a large amount of attenuation is acceptable because the flux would otherwise be high, the attenuation can now be converted into k-edge attenuation, which would further enhance the spectral separation.

Preferably the K-edge filter material has an element with an atomic number including 57 to 71.

Rotating Attenuation Elements

In another embodiment, the path-length of attenuating elements in the beam is modulated by rotating or rotating and translating the attenuating elements. FIG. 20A is a schematic illustration of an embodiment with a rotating attenuation element. A ray B passes through an attenuation element 2004 with a rectangular cross section with a width W. In this example, the ray B is parallel to the width of the attenuation element 2004, so that the path length of the ray B through the attenuation element 2004 is W. FIG. 20B is a schematic illustration where the attenuation element 2004 has been rotated around an axis of rotation 2008 an angle θ. The path length of the ray B through the attenuation element is now P=W/cos θ. Therefore, the path length of the ray through the attenuation element may be adjusted by rotating the attenuation element.

FIG. 20C is a cross-sectional view of the attenuation element 2004 through cut lines 20C. The cross-sectional slices of the attenuating element 2004 are tapered at the end, which in this embodiment forms a triangular cross-section. When the path-length of an individual attenuating element is plotted against fan-angle, the path-length should smoothly transition to zero (or at least fade to a small number close to zero), so as to minimize artifacts. Therefore, in this embodiment the attenuation element 2004 is a triangular prism.

To create customizable fluence fields, multiple attenuating elements would be used. The path-length introduced into the beam would be modulated as a function of the rotation. In this example, the path-length is modulated by the secant of the rotation angle.

Rotation has the advantage of being possibly easier to implement mechanically, because most motors begin with rotational motion which must be converted into translational motion. Also, for prism-like objects which do not change as a function of z, the rotating design has similar attenuation for different detector rows (i.e. different cone angle). This is not true with the translating design, which could either use a compensator to equalize the flux, or use alternating detector wedges which results in a modest efficiency reduction. Combinations of translations and rotations may be more advantageous than either motion alone.

In order to reduce the space needed, and possibly in order to realize other advantages (for example, faster or more uniform modulation rates), the attenuating wedges which are rotated may not be rods at all but might be curved. FIG. 21A shows one such example with attenuation element 2104, which is rotated around axis of rotation 2108. The path length of the ray B through the attenuation element 2104 is P1. FIG. 21B shows the attenuation element 2104 after it has been rotated around an axis of rotation 2108. The new path length is P2, which is greater than P1. The increase in P2 is dependent on the rotation angle, the bend of the attenuation element 2104 and the increase in the width of the attenuation element 2104.

A variation of this is to curve the wedges such that the minimum attenuation happens at the end, when the attenuating element is nearly removed from the beam. In this case, the attenuating element can be completely removed from the beam, resulting in a smooth transition to zero attenuation. This is useful for measurements when maximum flux is needed. If desired, a residual length of e.g. aluminum could be used to harden the beam slightly to reduce dose without significantly impacting the noise statistics.

Control Algorithms for Dynamic Attenuators

Dynamic attenuators, such as the piecewise-linear attenuator being disclosed here, are pre-patient beam shaping filters that modulate the distribution of x-ray fluence incident on the patient on a view-by-view basis. These attenuators can reduce dose while improving key image quality metrics such as peak or mean variance. In each view, the attenuator presents several degrees of freedom which may be individually adjusted. The total number of degrees of freedom across all views is very large, making many optimization techniques impractical. This embodiment provides methods for optimally controlling these attenuators.

The attenuator can be controlled to produce a distribution of flux onto the patient. The specification and claims describe such a distribution of flux, which is derived from the algorithms described here, as a "Hsieh-Pelc distribution."

These dynamic attenuators encompass a broad range of devices and not just the piecewise-linear attenuator, as described in J. S. Arenson, D. Ruimi, O. Meirav, R. H. Armstrong, General Electric Company, "X-ray flux management device," U.S. Pat. No. 7,330,535 (12 Feb. 2008); T. L. Toth, J. E. Tkaczyk, J. Hsieh, General Electric Company, "Method and apparatus of radiographic imaging with an energy beam tailored for a subject to be scanned," U.S. Pat. No. 7,076,029 (11 Jul. 2006), which are incorporated by reference for all purposes. Bowtie filters which translate or rotate and change their effective thickness as a function of such rigid motion can also be controlled by the methods described here. Dynamic attenuators which consist of two wedges which move into and out of the beam are also dynamic attenuators which may be controlled by the methods described below.

To derive the Hsieh-Pelc distribution, we will examine methods which minimize mean or peak variance subject to a fixed dose limit.

We will consider both systems with a perfect attenuator (i.e. any possible fluence profile can be achieved), and systems with more limited control. We will examine both solutions with knowledge of the patient anatomy, which may be determined from a pre-scan, and approximate solutions without this a priori knowledge.

Problem Definition

Let the system have M detector channels and let x be a vector with being the incident intensity for the $k^{th}$ ray in the sinogram. For k=M(i−1)+j, the $k^{th}$ ray $x_k$ corresponds to the $j^{th}$ detector channel in the $i^{th}$ view. $x_k$ is the x-ray illumination field, and is the key variable the dynamic attenuator controls. Our goal is to choose to optimize the image quality under a fixed dose limit.

Let $v_k$ be the photons detected in the $k^{th}$ ray, and let $f_k$ be the fraction of photons transmitted through the patient for the $k^{th}$ ray, so that $v_k = f_k x_k$. In most cases, we will use $f_k x_k$ instead of $v_k$ to make the relationship to explicit. We assume that $x_k$ is large enough to be noiseless. Assuming Poisson statistics (no electronic noise) and neglecting polychromatic effects, is then a Poisson random variable with mean and variance $$\mu_{v_k} = f_k x_k, \sigma_{v_k}^2 = f_k x_k \tag{1}$$

For CT reconstruction, the quantity of interest is log $f_k$, not $v_k$. Because $f_k$ is estimated using the basic relationship $f_k = v_k/x_k$, propagation of error can be used to show that $$\sigma_{f_k}^2 = v_k/x_k^2 \tag{2}$$

-continued $$\sigma_{\log f_k}^2 = \left(\frac{x_k}{v_k}\right)^2 \sigma_{f_k}^2 = (f_k x_k)^{-1}$$

In matrix form, let F be a diagonal matrix whose diagonal is $f$, so that $F_{kk}=f_k$. The detected intensity is then a vector with average value Fx and with variance $(Fx)^{-1}$, which is the component-wise reciprocal of Fx. We will assume a linear reconstruction algorithm and we will develop our algorithm for 2D scans using either analytic parallel beam or direct fan beam reconstruction.

In linear systems theory, filtered backprojection can be written as R=−A log F, with R being the reconstructed image in vector form and A being the mapping from the log-normalized measurements to the image via filtered backprojection (FBP). By propagation of error, the variance of the reconstructed image is $$\sigma_R^2 = (A \circ A)\sigma_{\log F}^2$$

$$\sigma_R^2 = (A \circ A)(Fx)^{-1} \quad (3)$$

Here, $A \circ A$ is the Hadamard product of A with itself and is simply the component-wise square of A. The variance in the image $\sigma_R^2$ can be well approximated by summing the variances in the rays that pass through the pixel, so that we can write $$\sigma^2 = cB(Fx)^{-1} \quad (4)$$

where B corresponds to the system matrix which sums all rays which pass through a pixel, and c is a constant that we will neglect. B is therefore a sparsified approximation to $A \circ A$. B itself is a backprojection without the filtering step, or "unfiltered backprojection." We assume a parallel-beam reconstruction here (or a rebin-to-parallel method), although the methods can be extended to fan beam reconstruction.

The optimization needs a dose metric to be controlled or minimized. We use the total energy absorbed, which is simply a dot product $$d^T x = \Sigma_k d_k \cdot x_k \quad (5)$$

The elements of $d_k$ are proportionality constants measuring the relative energy absorbed from the average photon delivered along the $k^{th}$ ray. A simple choice of $d_k$ is to set $d_k=1$ if the ray intersects the patient, and $d_k=0$ otherwise. This choice of $d_k$ measures entrance energy. A better choice of $d_k$ can be derived from Monte Carlo simulations. We will impose a limit of $d^T x = d_{tot}$ for all our optimization problems. This ensures that all systems will be compared at equal dose. Because variance and dose are inversely related (in the absence of electronic noise), any reduction seen in variance for equal dose can be equally well interpreted as a reduction in dose for equal variance.

System with the Perfect Attenuator
Weighted Mean Variance (WMV) Optimization

The weighted mean variance minimization problem is posed as

Minimize $\sigma^2 = w^T B(Fx)^{-1}$

Subject to $d^T x = d_{tot}$ (6)

$w^T$ is the row vector of voxel weights. In the simple mean variance optimization, $w_k=1$ for all voxels k which are clinically relevant, and $w_k=0$ for voxels which are not relevant (for example, which may occur outside the patient). The constraint $d^T x = d_{tot}$ enforces a dose limit on the system.

Looking more closely at Equation (6), we note that because the objective function is scalar, it may be transposed without modification: $(w^T B(Fx)^{-1})^T = (Fx)^T B^T w$. As B is the backprojection operator, $B^T$ is forward projection. In the unweighted case, if we assume that $w_k$ is one inside patient tissue and zero outside, $B^T w$ is the sinogram of the tissue path-lengths (the length of the intersection of the ray with the patient, not the line integral of attenuation).

Equation (6) can be solved using Lagrange multipliers. The solution is $$x_k = \sqrt{\frac{(B^T w)_k}{\lambda d_k F_{kk}}} \quad (7)$$

$\lambda$ is chosen in order to meet the dose constraint.

We note that if we use the entrance energy approximation for $d_k$ and if we ignore the variation in $B^T w$ and approximate it to be uniform, Equation (7) simplifies to $$x_k \propto \frac{1}{\sqrt{F_{kk}}} \quad (8)$$

This is consistent with previously derived theory for modulating the tube current.

Peak Variance Optimization

Optimization of mean variance may increase the variance in one region to obtain a reduction in another. In an extreme case, this could render part of the image nondiagnostic and a repeat scan may then be required. It is therefore desirable to reduce the peak variance of the image rather than the mean variance. We define the peak variance as the maximum variance of any voxel in the reconstruction. This problem is stated as Minimize $\sigma^2 = \max(B(Fx)^{-1})$ Subject to $d^T x = d_{tot}$ (9)

This is a minimax problem and does not easily admit a closed form solution. Because all engaged functions are convex, convex optimization techniques can be used to find an accurate numerical solution, but the computational load can be significant given the number of variables involved. However, it is clear that the problem is well-posed and that a solution exists. Let us call the optimized x to Equation (9) $x_{peak}$, and let $x_{peak}$ achieve optimized peak variance $\sigma_{minimax}^2 = \max B(Fx_{peak})^{-1}$. We note that the piecewise-linear attenuator can be thought of as a low-resolution approximation to the perfect attenuator.

Iterated Weighted Mean Variance (WMV) to Bound Peak Variance

Instead of solving for $x_{peak}$ directly, we can relate the optimized peak variance $\sigma_{minimax}^2$ to the solution to the WMV problem. Let us denote the choice of x which solves the WMV problem with weight $w^T$ as $x_{WMV}$. Let S be the set of all voxels k with strictly positive weight, that is, $w_k > 0$. We define two quantities $$\sigma_{maxWMV}^2 = \max(B(Fx_{WMV})^{-1}) \quad (10)$$

$$\sigma_{minWMV}^2 = \min_{k \in S} (B(Fx_{WMV})^{-1})_k$$

It can be shown that for any weight $w^T$, $$\sigma_{minWMV}^2 \leq \sigma_{minimax}^2 \leq \sigma_{maxWMV}^2 \quad (11)$$

Equations (10) and (11) suggest an alternative approach to solving the peak variance problem. Rather than optimizing peak variance directly, a WMV problem could be constructed which achieves a tight bound about the minimax variance. The upper bound $\sigma_{maxWMV}^2$ is the peak variance of the WMV solution. This simply states that the peak variance of the WMV solution cannot outperform the minimax variance. The lower bound $\sigma_{miniWMV}^2$ is the minimum variance of the WMV solution, but only of voxels which have strictly positive weight.

If a tight bound existed, Equations (10) and (11) predict that each voxel either attains the minimax variance with some positive weight, or outperforms the minimax variance but is assigned zero weight.

We therefore propose an iterative technique. The basic principle of the iterative technique is to increase, in each iteration, the weight for voxels with high noise and to decrease the weight for voxels with low noise.

We initialize $w^T=1^T$, solve the unweighted mean variance optimization problem, and initialize the step size to $c_{step}=1$. In each iteration, we perform the following steps:

1) Let S be the set of voxels with strictly positive weight, and sort the voxels of S in order of increasing variance. Create a function $g(\sigma_k^2)$ which smoothly maps the sorted variances of S uniformly to the range $[-1,1]$, and which uses linear interpolation or extrapolation if the variance $\sigma_k^2$ does not match the variance of any voxel in S.

2) Update the weight vector for each voxel as $w_k \to w_k e^{c_{step}g(\sigma_k^2)}$. This increases the weight for voxels with high noise, and decreases the weight for voxels with low noise. Any other mechanism which increases the weight of voxels with high noise and decreases the weight of voxels with low noise could be substituted for steps (1) and (2).

3) Decrease the step size using $c_{step} \to c_{decay}c_{step}$

4) Normalize the weight vector by dividing each element by the mean of w, setting $$w_k \to \frac{w_k}{\text{mean}(w)}.$$

Scaling the weight vector uniformly does not affect optimization but is only important for selecting voxels which should be set to zero weight in the next step.

5) If a voxel has a small weight so that $w_k < c_{cutoff}$, set $w_k \to 0$. If $w_k = 0$ and $g(\sigma_k^2) \geq 0$, then restore it by setting $w_k = c_{restore}$. The purpose of this step is only to increase the lower bound $\sigma_{miniWMV}^2$. We found that abruptly changing some $w_k$ can slow the rate of convergence for the upper bound $\sigma_{maxWMV}^2$.

6) Solve the WMV optimization problem using the updated weight vector.

We emphasize that any weight map $w^T$ will produce a bound on the minimax variance, and that more elegant methods for choosing $w^T$ can be constructed. In our experiments, we found that a method which simply decreases the weight of voxels with low variance and increases the weight of voxels with high variance, as this method does, will help to attain the minimax variance.

Systems with Limited Attenuators

We define the limited attenuator as an attenuator with a small number D degrees of freedom for each view. We assume the system is equipped with TCM (tube current modulation), so that it has a total of (D+1) degrees of freedom for each view. Across V views, the total number of degrees of freedom is (D+1) V. Since V is on the order of 1000, many general purpose optimization algorithms fail in finding the global minimum over (D+1)V variables. Our strategy is to decompose the problem into V separate optimization problems over D variables, instead of a single problem over (D+1)V variables.

Mean Variance Optimization

The mean variance minimization problem for this case is similar to Equation (6) but includes an additional constraint from the limits of the attenuator:

Minimize $\sigma_2 = 1^T B(Fx)^{-1}$

Subject to $d^T x = d_{tot}$ $$x_{M(i-1)+1, M(i-1)+2, \ldots, Mi} \in Q, i=1,2,\ldots V \quad (12)$$

Recall that M is the number of rays measured in each view. The 2D sinogram has MV entries. Q is an M-dimensional space that includes all allowed x-ray illumination fields for any single view. We assume tube current modulation such that if $Q_0 \in Q$, then $\alpha Q_0 \in Q$ for any $\alpha > 0$.

We decompose the problem into views. Let $S_i$ be the set of indices for rays in the $i^{th}$ view, and introduce auxiliary variables $x_{S_i}$ such that $$S_i = \{M(i-1)+1, M(i-1)+2, \ldots Mi-1, Mi\}$$

$$(x_{S_i})_k = \begin{cases} x_k, & k \in S_i \\ 0, & k \notin S_i \end{cases}$$

Let $d_{S_i}$ and $\sigma_{S_i}^2$ be the dose and total variance, respectively, associated with the $i^{th}$ view:

$$\sigma_{S_i}^2 = \sum_{k \in S_i} 1^T B \Delta_k (Fx)^{-1}$$

$$(\Delta_k)_{ij} = \begin{cases} 1, & i=j=k \\ 0, & \text{otherwise} \end{cases}$$

$$d_{S_i} = \sum_{k \in S_i} d_k x_k$$

Here, $\Delta_k$ is an auxiliary matrix that serves only to select the variance of the $k^{th}$ ray, and we set the variance of the remaining rays to zero. The problem in Equation (12) can be rewritten as Minimize $\sigma^2 = \Sigma_{i=1}^V \sigma_{S_i}^2$ Subject to $\Sigma_{i=1}^V d_{S_i} = d_{tot}$ $$x_{S_i} \in Q, i=1,2,\ldots V \quad (13)$$

We may now decouple the set of variables $S_i$ (the incident intensities) in each view. Note that the optimization problem for the perfect attenuator could also be decoupled into views, but this was not necessary because Lagrange multipliers could be employed directly. Suppose we are able to calculate the solution to the mean-variance problem within each view:

Minimize $\sigma_{S_i}^2$

Subject to $d_i = 1$ $$x_{S_i} \in Q \quad (14)$$

A solution to this problem with a dose limit of unity is directly proportional to the solution with any other dose limit because we can modulate the tube current. For the entire scan to be dose efficient, each view must be dose efficient.

This is a D-dimensional optimization problem, and may be solved with a number of optimization methods which are reliable with D dimensions but possibly not with (D+1)V dimensions. For D=1 or D=2, exhaustive search may be acceptable. Other methods include Neadler-Mead simplex search. Let the solution to the single-view illumination optimization problem, which consumes one unit of the allowed dose budget, be denoted as $\hat{x}_{S_i}$, and let the optimized $\sigma_{S_i}^2$ using $\hat{x}_{S_i}$ be $\omega_i$. In general, if the $i^{th}$ view consumes $d_{S_i}$ the dose budget, then, if optimized, it will contribute $\omega_i/d_{S_i}$ to the variance.

With individually optimized views, the only question remaining is how to choose the x-ray source current for each view. This can be determined with the following problem:

Minimize $\sigma^2 = \Sigma_{i=1}^{V} \omega i / d_{S_i}$

Subject to $\Sigma_{i=1}^{V} d_{S_i} = d_{tot}$ (15)

To allocate the dose distribution between different views, we again use Lagrange multipliers and find $$d_{S_i} = \sqrt{\frac{\omega_i}{\lambda}} \quad (16)$$

Therefore, to optimize the mean variance, the dynamic attenuator should be configured in each view to minimize the dose-variance product for that view, and the tube current should be adjusted such that the dose delivered in that view is proportional to the square root of the dose-variance product of that view.

Peak Variance Optimization

Peak variance optimization for the limited attenuator is a difficult problem because hundreds of degrees of freedom exist, and the problem is nonconvex. Stochastic techniques have been used in the past but do not provide guarantees on optimality. However, the iterated WMV developed for the perfect attenuator applies directly to the limited attenuator. The bound in Equation (11) still holds, with any solution to the WMV minimization providing a bound on the minimax variance.

Approximate Solutions without a Priori Knowledge

When a priori knowledge of the object transmission F is not available, heuristics must be used to approximately minimize image variance metrics. The elimination of the requirement for a priori knowledge makes these control methods more practical. In this section, we propose several methods for approximate control methods.

Mean Variance Optimization Using a Square-Root-Log Function

For mean variance optimization with the perfect attenuator, our solution was Equation (7), reproduced below for reference:

$$x_k = \sqrt{\frac{(B^T w)_k}{\lambda d_k F_{kk}}}$$

For simple mean variance optimization, w, the weight map, is 1 for any voxel of clinical relevance (tissue) and 0 otherwise. With a few approximations, this solution can be used as a real time control algorithm. If the patient shape can be roughly determined prior to the scan, e.g. from scout scans, $B^T w$ can be estimated by calculating the tissue path-length from the estimated patient shape. Alternatively, the patient can be modeled as being composed of uniformly attenuating material with linear attenuation coefficient $\mu$, choosing a value of $\mu$ representative of soft tissue. This approximation is sensible in regions of the body consisting mostly of soft tissue, but could cause problems in regions such as a thorax, with much of the lung tissue having a low $\mu$.

With the assumption that $(1^T B)_k$ is proportional the tissue path-length $l_k$, $F_{kk} = e^{-\mu l_k}$ and $$l_k = -\frac{\log(F_{kk})}{\mu} \quad (17)$$

We further assume that all rays which intersect the patient contribute equally to dose. Then Equation (7) simplifies to $$x_k \propto \sqrt{\log(F_{kk}^{-1}) F_{kk}^{-1}} \quad (18)$$

This expression depends only on the fraction of rays transmitted, $F_{kk}$, which can be well approximated using the previous view. If a more accurate model of dose were available, then the dependence on $d_k$ in Equation (7) could also be included. Similarly, dose sensitive organs can be protected by increasing $d_k$ for rays which are known to intersect these organs.

Power Law Control

An even simpler heuristic is to choose a power law. We have found good results with an exponent of −0.6, leading to the very simple expression $$x_k \propto F_{kk}^{-0.6} \quad (19)$$

For values of $F_{kk}^{-1}$ between 10 to 100, $F_{kk}^{-0.6}$ is quite similar to $\sqrt{\log(F_{kk}^{-1}) F_{kk}^{-1}}$, although at smaller $F_{kk}^{-1}$ (i.e. thin tissue path-lengths), $F_{kk}^{-0.6}$ delivers more flux. This makes the power law expression more robust than the square-root-log from Equation (18) in the thorax where the assumption of uniform attenuation is inaccurate.

Optimized Flat Variance for Peak Variance Minimization

For the task of peak variance optimization, one approach is to restrict ourselves to the minimal variance which is uniform (or flat) across the image. We will continue to assume that the dose metric is entrance energy.

It should be noted that the flat variance assumption is not always a good one. One example is the perfect attenuator scan of an annulus of water with an air core. Because this system is radially symmetric, it is feasible to cast this as a convex optimization problem and solve for the true solution $x_{peak}$ and $\sigma_{minimax}^2$ numerically. This can be compared to the solution which flattens the variance. We find that does not lead to a flat variance map. For an annulus with an inner radius of 10 cm, an outer radius of 30 cm and $\mu = 0.2$ cm$^{-1}$, $\sigma_{minimax}^2 \cong 0.86 \sigma_{flat}^2$, where $\sigma_{flat}^2$ is the variance if the perfect attenuator is controlled to equalize the variance in the reconstructed image everywhere. Using $x_{peak}$ results in reduced variance everywhere, both in the air core and water ring surrounding it.

However, the flat variance assumption simplifies the problem and reduces the requirements for a priori knowledge. The optimized flat variance problem is Minimize $\sigma_{flat}^2$ Subject to $d^T x = d_{tot}$ $$(B(Fx)^{-1})_k = \sigma_{flat}^2 \quad (20)$$

We will now appeal to an argument which is strictly true only in the continuous case and not the discretized problem as written. Because the variance map is flat everywhere, its Fourier transform has power only at the origin and the central slice theorem implies that the backprojected variance should be flat on a per-view basis. This in turn means that the variance of each measurement within each view should be equalized, so that $$f_k x_k = \alpha_k, k \in S_i \quad (21)$$

In the nearest-neighbor model of B, $\alpha_k$ is simply the variance delivered from each view. Although the variance must be flat within each view, it can vary from view to view. Choosing the optimal set of $\alpha_k$ can again be performed using Lagrange multipliers and yields $$\alpha_i \propto \sqrt{\sum_{k \in S_i} d_k x_k} \quad (22)$$

Therefore, within each view the detected number of photons should be constant, and the total dose delivered in each view should be modulated with the square root of the dose-variance product of that view.

These heuristics can be applied with minor modification to the piecewise-linear attenuator. Instead of using $f_k$ for a single ray, we use a single value for a block of $f_k$. In our simulations, we had one block per piecewise linear segment, with each block abutting its neighbors, and we used the harmonic mean of $f_k$ within the block instead of the arithmetic mean in order to increase the weight of highly attenuated rays.

When simulated on certain datasets, we find that these control methods can attain mean variance reductions of 15% and peak dose reductions of 30% when compared to the bowtie filter with perfect tube current modulation. These reductions in noise can be taken directly as reduction in dose if the tube current is reduced. The benefits may be greater on other datasets.

These embodiments are further described in "Control Algorithms For Dynamic Attenuators" by SS Hsieh and NJ Pelc, in Med. Phys. 2014 June; 41(6):061907, which may also be found at http://www.ncbi.nlm.nih.gov/pubmed/24877818.

Gas-Filled Attenuators

Another embodiment provides a gas-filled attenuator. This would consist of a series of chambers which are placed between the source and object. Each chamber can be compressed or decompressed, with the goal of modulating the pressure of the gas during the scan. By increasing the pressure of the gas, a greater attenuation would be presented by a chamber to the patient.

Possible candidate gases include Xe, Kr, or any other gas with a high molecular weight or atomic number. Ideally, the chosen chemical would be a gas at typical temperatures and at high pressures.

The shape of these chambers should be such that sharp edges in attenuation are not presented to the detector, which would lead to difficulties in reconstruction. For example, if the chambers are trapezoids, or if they are rotated rectangular prisms, then the attenuation plotted as a function of fan angle will not have sharp discontinuities.

Gas detectors have a long history in x-ray CT imaging. These detectors obviously have significant stopping power, and our gas-filled dynamic attenuator would operate with similar principles, except that it would be dynamically controlled during the scan to modulate the x-ray radiation intensity.

Figure 22:
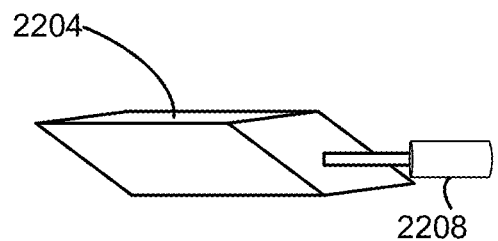
FIG. 22 is a perspective view of an element of a bowtie filter, which uses a gas filled attenuator.

FIG. 22 is a perspective view of an element 2204 of a bowtie filter, which uses a gas filled attenuator. In this example, the element 2204 is a chamber in the shape of a right or oblique prism with a parallelogram shaped base. In other embodiments, the base may be triangular. In other embodiments, the chamber may have other shapes. Preferably, the base or shape of the element 2204 allows overlapping between adjacent elements in the bowtie filter to reduce or prevent sharp edges for filtering. A pressure controller 2208 is in fluid connection with the element 2204 to control gas pressure within the element. The element 2204 is filled with a high molecular weight gas with a molecular weight greater than 83 amu. Such a gas may be Xe, Kr, or $XeF_4$. The pressure controller 2208 is able to provide the gas at a pressure up to at least 10 atmospheres. By changing the gas pressure, the attenuation of the element 2204 may be changed. The pressure controller 2208 is able to quickly regulate the pressure in the element 2204 during the CT scan. For example, a pressure controller 2208 may have the ability to provide a pressure between 1 atm and 50 atm. This allows the pressure controller 2208 to increase attenuation by 50 times from lowest to highest attenuation. Preferably, the pressure controller 2208 is able to regulate the pressure in the element 2204 with a speed sufficient to allow gantry orientations between successive rotation to have a set pressure profile and allow different orientations during a single rotation to have different pressure profiles.

Liquid-Filled Attenuators

An alternative embodiment is a liquid attenuator. This would consist of a series of small chambers which could be individually emptied or filled in order to customize the x-ray fluence profile. Different forms of fluid control could be used. For example, the paper "Fluid Control in Multichannel Structures by Electrocapillary Pressure" (Prins, Welters, Weekamp 2012) documents control of fluid motion using thousands of microchannels using electrocapillary pressure, and with velocities of several cm per second. Other possibilities exist for rapid fluid control.

The liquid would be chosen to be highly attenuating. One example is iodinated solution. Another possibility is a suspension of particles with high atomic number into some other liquid.

The arrangement would have to be chosen such that sharp edges do not present themselves in the attenuation profile. One other possibility is to place the chambers end-on in the direction of the travel of the x-ray source, perhaps with some tilt such that the shadow through a filled chamber is spread out over several detector channels instead of a single one to avoid sharp edges. Then, the length of the chambers could be in powers of two (e.g. lengths of 1 mm, 2 mm, 4 mm, 8 mm) so that the desired thickness of attenuator could be encoded with binary.

Figure 23:
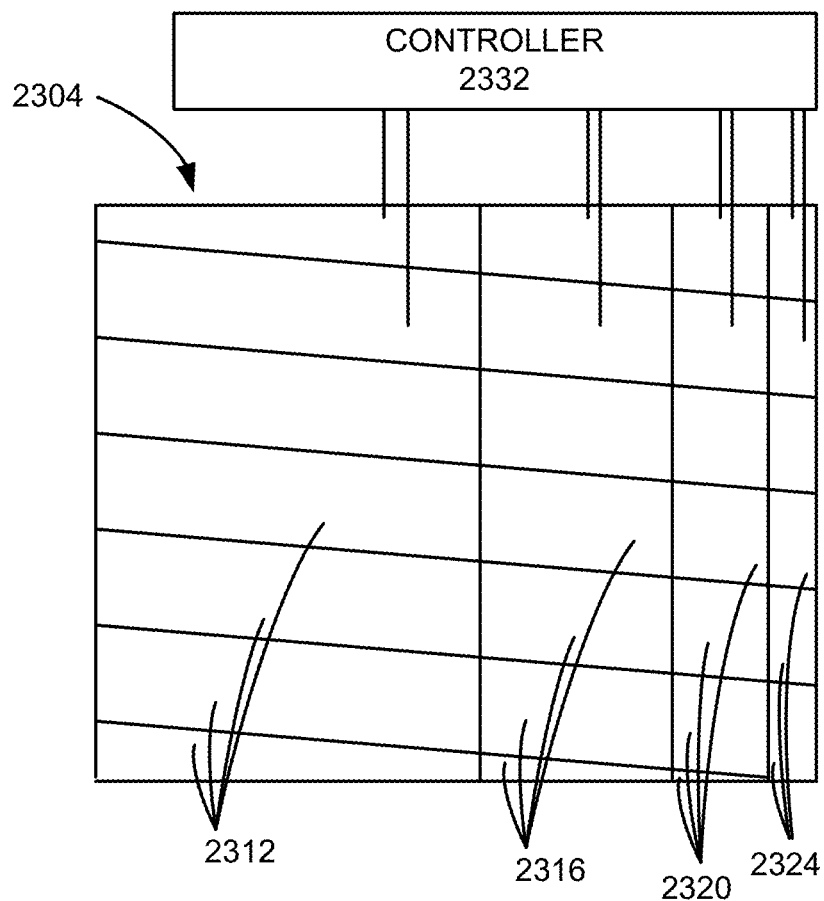
FIG. 23 is a top view of an element of a bowtie filter 2304, which uses a liquid filled attenuator.

FIG. 23 is a top view of an element of a bowtie filter 2304, which uses a liquid filled attenuator. In this example the element of the bow tie filter 2304 comprises a plurality of chambers 2312, 2316, 2320, 2324. Each of the plurality of chambers 2312, 2316, 2320, 2324 is in fluid connection with a fluid controller 2332. The fluid controller 2332 may be a single control unit or several control units. For example, there may be an individual control unit for each individual chamber. The liquid controller 2332 is able to quickly fill or empty the chambers 2312, 2316, 2320, 2324. By controlling which chambers 2312, 2316, 2320, 2324 are filled or empty the liquid controller 2332 is able to control the attenuation profile of the bowtie filter 2304. Preferably, the liquid controller 2332 is able to regulate the liquid in the bowtie filter 2304 with a speed sufficient to allow gantry orientations between successive rotation to have a set attenuation profile and allow different orientations during a single rotation to have different attenuation profiles.

In this example the walls are angled with respect to the direction of a x-ray beam to reduce or eliminate sharp edges. In addition in this example, thicknesses of first chambers 2312 are twice the thickness of second chambers 2316. Second chambers 2316 have a thickness twice that of the thickness of third chambers 2320. Third chambers 2320 have a thickness twice the thickness of fourth chambers 2324. This allows for binary addition of the different chamber thicknesses, by filling different chambers with a liquid to obtain different attenuation thicknesses.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A CT apparatus for scanning an object, comprising:
    an x-ray source, wherein the x-ray source provides a collimated x-ray beam with a cross-section with a length and thickness;
    a plurality of filter elements comprising a K-edge filter material between the source and object, wherein the K-edge filter material provides a K-edge above 20 KeV;
    an actuator connected to a filter element of the plurality of filter elements for moving the filter element to change a cross-sectional path length of the collimated x-ray beam through the filter element;
    an x-ray detector on an opposite side of the object from the x-ray source for detecting x-rays that pass through the object and the plurality of filter elements; and
    a gantry for rotating the x-ray source, the plurality of filter elements, and the x-ray detector around an axis of rotation, wherein the actuator moves the filter element of the plurality of filter elements in a direction of movement substantially parallel to the axis of rotation and wherein each filter element of the plurality of filter elements is a wedge that increases or decreases in thickness along the direction of movement and wherein the length of the cross-section is defined as being perpendicular to the direction of movement wherein thicknesses of each filter element of the plurality of filter elements change in a direction along the length of the cross-section of the collimated x-ray beam which is perpendicular to the direction of movement and wherein the thicknesses of the filter elements increase or decrease in a direction that is perpendicular to the direction of movement and the length of the cross-section of the collimated x-ray beam.

2. The CT apparatus, as recited in claim 1, wherein the K-edge filter material is an element with an atomic number between and including 57 to 71.

3. The CT apparatus, as recited in claim 2, wherein the thicknesses of the wedges alternately increase and decrease in a direction along the length of the cross-section of the collimated x-ray beam.

4. The CT apparatus, as recited in claim 1, wherein the x-ray beam has a spectrum and wherein the K-edge is within the spectrum of the x-ray beam.

5. The CT apparatus, as recited in claim 1, wherein the each filter element provides an attenuation, wherein a profile of the attenuation is approximately a power law of an attenuation of the object being scanned.

6. The CT apparatus, as recited in claim 1, wherein the each filter element provides an attenuation where a profile of the attenuation is approximately a power law of an attenuation of the object being scanned, divided by the logarithm of the attenuation of the object being scanned.

7. A CT apparatus for scanning an object, comprising:
    an x-ray source, wherein the x-ray source provides a collimated x-ray beam with a cross-section with a length and thickness and a direction of travel;
    a plurality of attenuating elements between the source and object;
    an actuator system connected to each attenuating element of the plurality of attenuating elements for individually rotating a plurality of attenuating elements, wherein the rotation changes path lengths of the x-ray beam through each attenuating element of the plurality of attenuating elements, wherein the attenuating elements have tapered edges, wherein thicknesses of the attenuating elements change in a direction along the length of the cross-section of the collimated x-ray beam due to the tapered edges, wherein the tapered edges smoothly transition to zero;
    an x-ray detector on an opposite side of the object from the x-ray source for detecting x-rays that pass through the object and the plurality of attenuating elements; and
    a gantry for rotating the x-ray source, the plurality of attenuating elements, and the x-ray detector around an axis of rotation.

8. The CT apparatus, as recited in claim 7, wherein the attenuating elements have a length and wherein rotating each attenuating element rotates each attenuating element around an axis of rotation, wherein the axis of rotation is not parallel to the direction of travel of the collimated x-ray beam and is not parallel to the length of the attenuating elements.

9. The CT apparatus, as recited in claim 8, wherein the plurality of attenuating elements are positioned so that some directions of travel of the x-ray beam pass through more than one attenuating element.

10. The CT apparatus, as recited in claim 9, wherein the axis of rotation is perpendicular to the direction of travel of the collimated x-ray beam.

11. The CT apparatus, as recited in claim 10, wherein the axis of rotation is perpendicular to the length of an attenuating element.

12. A CT apparatus for scanning an object, comprising:
    an x-ray source, wherein the x-ray source provides a collimated x-ray beam with a cross-section with a length and thickness;
    a plurality of filter elements comprising gas filled chambers;

a pressure controller for controlling gas pressures in the plurality of filter elements, wherein the pressure controller is able to provide different pressures in different filter elements of the plurality of filter elements, wherein the gas pressures are used to control attenuation;

an x-ray detector on an opposite side of the object from the x-ray source for detecting x-rays that pass through the object and the plurality of filter elements; and a gantry for rotating the x-ray source, the plurality of filter elements, and the x-ray detector around an axis of rotation, wherein the filter element of the plurality of filter elements increases or decreases in thickness along a first direction perpendicular to the axis of rotation and increases or decreases in thickness along a second direction perpendicular to the axis of rotation and the first direction.

13. The CT apparatus, as recited in claim 12, wherein the pressure controller is able to change pressure during a CT scan.

14. The CT apparatus, as recited in claim 13, wherein the pressure controller is able to change pressure during rotations of the gantry, wherein a gantry orientation between successive rotations may provide a set pressure profile and different gantry orientations during a single rotation provide different pressure profiles.

15. The CT apparatus, as recited in claim 12, wherein the plurality of filter elements overlap in a directions extending from the source to the x-ray detectors to prevent sharp edges.

16. The CT apparatus, as recited in claim 12, wherein the chambers are right or oblique prisms.

17. The CT apparatus, as recited in claim 16, wherein the right or oblique prisms have overlapping triangular or parallelogram bases.

18. The CT apparatus, as recited in claim 12, wherein the filter elements are filled with a high molecular weight gas, wherein the high molecular weight gas has a molecular weight greater than 83 amu.

19. The CT apparatus, as recited in claim 12, wherein the filter elements are filled with at least one of Xe, Kr, or $XeF_4$.

20. The CT apparatus, as recited in claim 12, wherein the pressure controller is able to provide a pressure of at least 10 atmospheres.

21. A CT apparatus for scanning an object, comprising:
an x-ray source, wherein the x-ray source provides a collimated x-ray beam with a cross-section with a length and thickness;

a plurality of filter elements wherein each filter element comprises at least one hollow chamber;

a liquid controller, which is able to fill and empty the plurality of filter elements with a liquid;

an x-ray detector on an opposite side of the object from the x-ray source for detecting x-rays that pass through the object and the plurality of filter elements; and a gantry for rotating the x-ray source, the plurality of filter elements, and the x-ray detector around an axis of rotation, wherein each filter element of the plurality of filter elements increases or decreases in thickness along a first direction perpendicular to the axis of rotation and increases or decreases in thickness along a second direction perpendicular to the axis of rotation and the first direction.

22. The CT apparatus, as recited in claim 21, wherein the liquid controller controls attenuation by filling or emptying the plurality of filter elements.

23. The CT apparatus, as recited in claim 21, wherein the liquid controller is able to change empty and fill filter elements during rotations of the gantry, wherein a gantry orientation between successive rotations may provide a set fill profile and different gantry orientations during a single rotation provide different fill profiles.

24. The CT apparatus, as recited in claim 21, wherein the plurality of filter elements overlap in a directions extending from the source to the x-ray detectors to prevent sharp edges.

* * * * *